(12) United States Patent
Fischer et al.

US008293467B2

(10) Patent No.: US 8,293,467 B2
(45) Date of Patent: Oct. 23, 2012

(54) BIOLOGICAL SPECIMEN COLLECTION AND TRANSPORT SYSTEM AND METHODS OF USE

(75) Inventors: Gerald W. Fischer, Bethesda, MD (US); Luke T. Daum, San Antonio, TX (US)

(73) Assignee: Longhorn Vaccines & Diagnostics LLC, San Antonio, TX (US)

( * ) Notice: Subject to any disclaimer, the term of this patent is extended or adjusted under 35 U.S.C. 154(b) by 0 days.

(21) Appl. No.: 13/332,204

(22) Filed: Dec. 20, 2011

(65) Prior Publication Data

US 2012/0100529 A1   Apr. 26, 2012

Related U.S. Application Data

(63) Continuation of application No. 12/243,949, filed on Oct. 1, 2008, now Pat. No. 8,084,443.

(60) Provisional application No. 60/976,728, filed on Oct. 1, 2007.

(51) Int. Cl.
 *C12Q 1/70* (2006.01)
 *C12Q 1/68* (2006.01)
(52) U.S. Cl. .......................................... 435/5; 435/6.12
(58) Field of Classification Search ............. 435/5, 6.12
 See application file for complete search history.

(56) References Cited

U.S. PATENT DOCUMENTS

| | | | |
|---|---|---|---|
| 4,116,777 A | 9/1978 | Takátsy et al. | |
| 4,196,265 A | 4/1980 | Koprowski et al. | |
| 4,235,244 A | 11/1980 | Abele et al. | |
| 4,315,073 A | 2/1982 | Brown et al. | |
| 4,355,102 A | 10/1982 | Quash | |
| 4,356,170 A | 10/1982 | Jennings et al. | |
| 4,372,945 A | 2/1983 | Likhite | |
| 4,474,757 A | 10/1984 | Arnon et al. | |
| 4,529,702 A | 7/1985 | Bryan | |
| 4,554,101 A | 11/1985 | Hopp | |
| 4,559,231 A | 12/1985 | Bjerre et al. | |
| 4,578,770 A | 3/1986 | Mitani | |
| 4,588,680 A | 5/1986 | Bucher et al. | |
| 4,596,792 A | 6/1986 | Vyas | |
| 4,599,230 A | 7/1986 | Milich et al. | |
| 4,601,903 A | 7/1986 | Frasch | |
| 4,608,251 A | 8/1986 | Mia | |
| 4,634,664 A | 1/1987 | Oestberg | |
| 4,634,666 A | 1/1987 | Engleman et al. | |
| 4,668,476 A | 5/1987 | Bridgham et al. | |
| 4,683,195 A | 7/1987 | Mullis et al. | |
| 4,683,202 A | 7/1987 | Mullis | |
| 4,707,450 A | 11/1987 | Nason | |
| 4,744,982 A | 5/1988 | Hunter et al. | |
| 4,746,490 A | 5/1988 | Saneii | |
| 4,749,490 A | 6/1988 | Smyth et al. | |
| 4,800,159 A | 1/1989 | Mullis et al. | |
| 4,803,998 A | 2/1989 | Kezes et al. | |
| 4,816,513 A | 3/1989 | Bridgham et al. | |
| 4,883,750 A | 11/1989 | Whiteley et al. | |
| 4,954,449 A | 9/1990 | Hunter et al. | |
| 4,981,782 A | 1/1991 | Judd et al. | |
| 4,996,143 A | 2/1991 | Heller et al. | |
| 5,091,316 A | 2/1992 | Monthony et al. | |
| 5,108,927 A | 4/1992 | Dorn | |
| 5,136,019 A | 8/1992 | Judd et al. | |
| 5,145,684 A | 9/1992 | Liversidge et al. | |
| 5,149,653 A | 9/1992 | Roser | |
| 5,163,441 A | 11/1992 | Monthony et al. | |
| 5,182,109 A | 1/1993 | Tamura et al. | |
| 5,186,898 A | 2/1993 | Bridgham et al. | |
| 5,187,060 A | 2/1993 | Cerutti et al. | |
| 5,234,809 A | 8/1993 | Boom | |
| 5,243,030 A | 9/1993 | Judd et al. | |
| 5,252,458 A | 10/1993 | Liav et al. | |
| 5,290,686 A | 3/1994 | Kendal et al. | |
| 5,316,910 A | 5/1994 | Rota et al. | |
| 5,399,363 A | 3/1995 | Liversidge et al. | |
| 5,482,856 A | 1/1996 | Fell, Jr. et al. | |
| 5,503,841 A | 4/1996 | Doyle et al. | |
| 5,543,158 A | 8/1996 | Gref et al. | |
| 5,545,555 A | 8/1996 | Racioppi et al. | |
| 5,552,157 A | 9/1996 | Yagi et al. | |
| 5,565,213 A | 10/1996 | Nakamori et al. | |
| 5,565,322 A | 10/1996 | Heller | |
| 5,567,434 A | 10/1996 | Szoka, Jr. | |
| 5,571,511 A | 11/1996 | Fischer | |
| 5,589,174 A | 12/1996 | Okuno et al. | |
| 5,627,071 A | 5/1997 | Triva | |
| 5,631,350 A | 5/1997 | Okuno et al. | |
| 5,641,515 A | 6/1997 | Ramtoola | |
| 5,656,016 A | 8/1997 | Ogden | |
| 5,663,055 A | 9/1997 | Turner et al. | |
| 5,679,356 A | 10/1997 | Bonnem et al. | |
| 5,691,299 A | 11/1997 | Fabry | |
| 5,697,899 A | 12/1997 | Hillman et al. | |
| 5,702,944 A | 12/1997 | Racioppi et al. | |
| 5,719,020 A | 2/1998 | Liav et al. | |
| 5,738,868 A | 4/1998 | Shinkarenko | |

(Continued)

FOREIGN PATENT DOCUMENTS

EP    0 313 224 A1    4/1989

(Continued)

OTHER PUBLICATIONS

U.S. Appl. No. 12/426,890, filed Sep. 17, 2009, Fischer et al.

(Continued)

*Primary Examiner* — Raymond Henley, III
(74) *Attorney, Agent, or Firm* — Remenick PLLC

(57) ABSTRACT

Disclosed are compositions for isolating populations of nucleic acids from biological, forensic, and environmental samples. Also disclosed are methods for using these compositions as one-step formulations for killing pathogens, inactivating nucleases, and releasing polynucleotides from other cellular components within the sample, and stabilizing the nucleic acids prior to further processing or assay. The disclosed compositions safely facilitate rapid sample collection, and provide extended storage and transport of the samples at ambient or elevated temperature without contamination of the sample or degradation of the nucleic acids contained therein. This process particularly facilitates the collection of specimens from remote locations, and under conditions previously considered hostile for preserving the integrity of nucleic acids released from lysed biological samples without the need of refrigeration or freezing prior to molecular analysis.

42 Claims, 19 Drawing Sheets

U.S. PATENT DOCUMENTS

| | | | |
|---|---|---|---|
| 5,741,516 A | 4/1998 | Webb et al. |
| 5,766,841 A | 6/1998 | Liav et al. |
| 5,770,219 A | 6/1998 | Chiang et al. |
| 5,779,708 A | 7/1998 | Wu |
| 5,783,208 A | 7/1998 | Venkateshwaran et al. |
| 5,785,975 A | 7/1998 | Parikh |
| 5,795,582 A | 8/1998 | Wright |
| 5,795,587 A | 8/1998 | Gao et al. |
| 5,797,898 A | 8/1998 | Santini, Jr. et al. |
| 5,800,810 A | 9/1998 | Doyle et al. |
| 5,849,489 A | 12/1998 | Heller |
| 5,891,624 A | 4/1999 | Huang |
| 5,945,515 A | 8/1999 | Chomczynski |
| 5,955,074 A | 9/1999 | Fischer |
| 5,958,379 A | 9/1999 | Regenold et al. |
| 6,015,664 A | 1/2000 | Henrickson et al. |
| 6,033,673 A | 3/2000 | Clements |
| 6,060,068 A | 5/2000 | Doyle et al. |
| 6,136,585 A | 10/2000 | Ball et al. |
| 6,162,603 A | 12/2000 | Heller |
| 6,168,915 B1 | 1/2001 | Scholl et al. |
| 6,242,582 B1 | 6/2001 | Reece et al. |
| 6,280,928 B1 | 8/2001 | Scholl et al. |
| 6,306,404 B1 | 10/2001 | LaPosta et al. |
| 6,306,582 B1 | 10/2001 | Scholl et al. |
| 6,312,395 B1 | 11/2001 | Tripp et al. |
| 6,376,172 B1 | 4/2002 | Scholl et al. |
| 6,406,842 B2 | 6/2002 | Scholl et al. |
| 6,440,423 B1 | 8/2002 | Clements et al. |
| 6,451,325 B1 | 9/2002 | Van Nest et al. |
| 6,458,577 B1 | 10/2002 | Huang |
| 6,495,316 B1 | 12/2002 | Scholl et al. |
| 6,500,432 B1 | 12/2002 | Dalemans et al. |
| 6,503,745 B1 | 1/2003 | Chand et al. |
| 6,534,065 B1 | 3/2003 | Makin et al. |
| 6,572,866 B1 | 6/2003 | Torcia |
| 6,573,080 B2 | 6/2003 | Scholl et al. |
| 6,602,510 B1 | 8/2003 | Fikes et al. |
| 6,603,908 B2 | 8/2003 | Dallas et al. |
| 6,603,998 B1 | 8/2003 | King et al. |
| 6,610,293 B1 | 8/2003 | Fischer et al. |
| 6,610,474 B1 | 8/2003 | Huang |
| 6,627,396 B1 | 9/2003 | Swanson et al. |
| 6,632,432 B1 | 10/2003 | Fischer |
| 6,680,308 B1 | 1/2004 | Hassan |
| 6,689,363 B1 | 2/2004 | Sette et al. |
| 6,713,068 B1 | 3/2004 | Audonnet et al. |
| 6,720,409 B2 | 4/2004 | Okuno et al. |
| 6,734,292 B1 | 5/2004 | Omura et al. |
| 6,759,241 B1 | 7/2004 | Hone et al. |
| 6,780,421 B1 | 8/2004 | Haensler et al. |
| 6,793,928 B1 | 9/2004 | van Scharrenburg et al. |
| 6,811,971 B2 | 11/2004 | Klepp et al. |
| 6,855,321 B1 | 2/2005 | Rappuoli et al. |
| 6,875,600 B2 | 4/2005 | Scholl et al. |
| 6,881,835 B2 | 4/2005 | Bai et al. |
| 6,893,814 B2 | 5/2005 | Swanson et al. |
| 6,939,543 B2 | 9/2005 | Fischer et al. |
| 6,946,291 B2 | 9/2005 | Scholl et al. |
| 7,090,853 B2 | 8/2006 | Kapp et al. |
| 7,223,409 B2 | 5/2007 | Nagata et al. |
| 7,279,162 B1 | 10/2007 | Fischer |
| 7,311,671 B2 | 12/2007 | Jung et al. |
| 7,351,413 B2 | 4/2008 | Page et al. |
| 7,357,936 B1 | 4/2008 | Garcon |
| 7,361,352 B2 | 4/2008 | Birkett et al. |
| 7,438,919 B2 | 10/2008 | Dowling et al. |
| 7,494,771 B2 | 2/2009 | Picard et al. |
| 7,541,194 B2 | 6/2009 | Mink et al. |
| 7,547,512 B2 | 6/2009 | Peiris |
| 7,648,681 B2 | 1/2010 | Meyer et al. |
| 7,718,402 B2 | 5/2010 | Gayral et al. |
| 7,794,001 B2 | 9/2010 | Blackwell et al. |
| 8,080,645 B2 | 12/2011 | Fischer et al. |
| 8,084,443 B2 | 12/2011 | Fischer et al. |
| 8,097,419 B2 | 1/2012 | Fischer et al. |
| 2001/0021501 A1 | 9/2001 | Scholl et al. |
| 2001/0034022 A1 | 10/2001 | Scholl et al. |
| 2001/0036628 A1 | 11/2001 | Scholl et al. |
| 2002/0054882 A1 | 5/2002 | Okuno et al. |
| 2002/0055094 A1 | 5/2002 | Reece et al. |
| 2002/0081567 A1 | 6/2002 | Henrickson et al. |
| 2002/0082395 A1 | 6/2002 | Fischer et al. |
| 2002/0169140 A1 | 11/2002 | Prendergast |
| 2003/0119209 A1 | 6/2003 | Kaylor et al. |
| 2003/0203357 A1 | 10/2003 | Huang |
| 2003/0215796 A1 | 11/2003 | Scholl et al. |
| 2003/0219442 A1 | 11/2003 | Mikayama et al. |
| 2004/0009126 A1 | 1/2004 | Pilkiewicz et al. |
| 2004/0013673 A1 | 1/2004 | Fischer et al. |
| 2004/0071757 A1 | 4/2004 | Rolf |
| 2004/0082549 A1 | 4/2004 | Jomaa |
| 2004/0086849 A1 | 5/2004 | Shimasaki et al. |
| 2004/0126789 A1 | 7/2004 | Park et al. |
| 2004/0142319 A1 | 7/2004 | Yu et al. |
| 2004/0170965 A1 | 9/2004 | Scholl et al. |
| 2004/0214272 A1 | 10/2004 | La Rosa et al. |
| 2004/0223976 A1 | 11/2004 | Bianchi et al. |
| 2005/0009008 A1 | 1/2005 | Robinson et al. |
| 2005/0042229 A1 | 2/2005 | Yang et al. |
| 2005/0090009 A1 | 4/2005 | Cormier et al. |
| 2005/0169941 A1 | 8/2005 | Lees |
| 2005/0170334 A1 | 8/2005 | Mikayama et al. |
| 2005/0181357 A1 | 8/2005 | Peiris et al. |
| 2005/0187213 A1 | 8/2005 | Lang et al. |
| 2005/0227269 A1 | 10/2005 | Lloyd et al. |
| 2006/0002939 A1 | 1/2006 | Fischer et al. |
| 2006/0014185 A1 | 1/2006 | Ollikka et al. |
| 2006/0105468 A1 | 5/2006 | Winkler et al. |
| 2006/0121468 A1 | 6/2006 | Allnutt et al. |
| 2006/0286557 A1 | 12/2006 | Basehore et al. |
| 2007/0102946 A1 | 5/2007 | Blackwell et al. |
| 2007/0172835 A1 | 7/2007 | McBride et al. |
| 2007/0196388 A1 | 8/2007 | Dowling et al. |
| 2007/0202497 A1 | 8/2007 | Renuart et al. |
| 2007/0202511 A1 | 8/2007 | Chen et al. |
| 2007/0286871 A1 | 12/2007 | Hickle et al. |
| 2008/0032921 A1 | 2/2008 | Alexander et al. |
| 2008/0050737 A1 | 2/2008 | Arieli et al. |
| 2008/0069821 A1 | 3/2008 | Yang et al. |
| 2008/0075708 A1 | 3/2008 | Yu et al. |
| 2008/0107665 A1 | 5/2008 | Suckow et al. |
| 2008/0107687 A1 | 5/2008 | Poulet |
| 2008/0118531 A1 | 5/2008 | Hoffmann et al. |
| 2008/0139789 A1 | 6/2008 | Fischer |
| 2008/0145373 A1 | 6/2008 | Arumugham et al. |
| 2008/0181914 A1 | 7/2008 | Eichhorn |
| 2008/0260763 A1 | 10/2008 | Felgner et al. |
| 2009/0081202 A1 | 3/2009 | Fischer et al. |
| 2009/0098527 A1 | 4/2009 | Fischer et al. |
| 2009/0233309 A1 | 9/2009 | Fischer et al. |
| 2009/0312285 A1 | 12/2009 | Fischer et al. |
| 2010/0009343 A1 | 1/2010 | Fischer et al. |
| 2010/0055672 A1 | 3/2010 | Saghbini |
| 2010/0221822 A1 | 9/2010 | Fischer et al. |
| 2011/0281754 A1 | 11/2011 | Fischer et al. |
| 2012/0088231 A1 | 4/2012 | Fischer et al. |
| 2012/0100529 A1 | 4/2012 | Fischer et al. |
| 2012/0107799 A1 | 5/2012 | Daum |
| 2012/0115126 A1 | 5/2012 | Fischer et al. |

FOREIGN PATENT DOCUMENTS

| | | |
|---|---|---|
| EP | 320308 | 6/1989 |
| EP | 0 621 339 A2 | 10/1994 |
| EP | 0 675 199 A2 | 10/1995 |
| EP | 0 726 316 A2 | 8/1996 |
| EP | 1 081 496 A1 | 3/2001 |
| RU | 2150281 C1 | 10/2000 |
| WO | WO 92/03454 | 3/1992 |
| WO | WO 92/16619 | 10/1992 |
| WO | WO 94/09035 | 4/1994 |
| WO | WO 94/17106 | 8/1994 |
| WO | WO 95/08348 | 3/1995 |
| WO | WO 97/05248 A2 | 2/1997 |
| WO | WO 97/46707 | 12/1997 |
| WO | WO 97/46712 | 12/1997 |
| WO | WO 97/46714 | 12/1997 |

| | | |
|---|---|---|
| WO | WO01/16163 | 8/2001 |
| WO | WO 03/053462 | 3/2003 |
| WO | WO 03/026567 A2 | 4/2003 |
| WO | WO 2004/004658 A2 | 1/2004 |
| WO | WO 2004/043407 | 5/2004 |
| WO | WO 2004/055205 | 7/2004 |
| WO | WO2004/002451 | 8/2004 |
| WO | WO 2004/072270 A1 | 8/2004 |
| WO | WO 2004/084876 A2 | 10/2004 |
| WO | WO 2005/075642 A1 | 8/2005 |
| WO | WO 2005/085274 A1 | 9/2005 |
| WO | WO2006/041933 | 4/2006 |
| WO | WO 2006/138444 | 12/2006 |
| WO | WO 2007/051036 | 3/2007 |
| WO | WO 2007/056266 | 5/2007 |
| WO | WO2007051036 | 5/2007 |
| WO | WO2007056266 | 5/2007 |
| WO | WO 2007/091030 | 8/2007 |
| WO | WO 2007/133682 | 11/2007 |
| WO | WO2008079463 | 3/2008 |
| WO | WO2008079463 | 7/2008 |
| WO | WO2009085355 | 7/2009 |
| WO | WO2009085355 | 9/2009 |

OTHER PUBLICATIONS

U.S. Appl. No. 13/328,992, Fischer et al.
U.S. Appl. No. 12/243,949, filed Oct. 1, 2008, Fischer.
U.S. Appl. No. 12/510,968, filed Jul. 28, 2009, Fischer.
Buck et al. BioTechniques vol. 27, pp. 528-536, Sep. 1999.
Characterization of Novel Influenza 2005.
Daum, et al., Abstract and Poster—"Development of a Real Time Reverse-Transcription PCR (RRT-PCR) Assay for Detection of Influenza a H1N1 2009 from Clinical Respiratory Specimens," Pediatric Infectious Disease Conference ESPID, Nice, France, May 5-8, 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Hindiyeh et al. Journal of Clinical Microbiology, vol. 43, No. 2, pp. 589-595, Feb. 2005.
"Adamantane Resistance Among Influenza, etc.", JAMA, Feb. 22, 2006, vol. 295, No. 8, pp. 891-894.
Kutyavin et al. 3'-Minor groove binder-DNA probes increase sequence specificity at PCR extension temperatures. Nucleic Acid Res. (2000) vol. 28, No. 2, pp. 655-661.
Lowe et al. A computer program for selection of oligonucleotide primers for polymerase chain reactions. Nucleic Acids Research (1990) vol. 18, No. 7, pp. 1757-1761.
Denhart, M., and Doraiswamy, V., "Master Your PCR Domain!" Promega Notes, 78: 9-12 (2001).
Master Your PCR Domain.
http://www.ncbi.nim.nih.gov/genomes/FLU/SwineFlu2009.html.
NCBI Influenza Virus Resource "CLE I. GenBank Sequence from Pandemic (H1N1) 2009 Viruses". 1237 pages.
Pamphlet—"Prime PCR System"—Longhorn Vaccines & Disagnostics.
Magari, R.T., Assessing shelf life using real-time and accelerated stability tests, BioPharm Nov. 2003.
"Taq PCR Master Mix (2x)," USB Corp., (2007).
"Immunoflourescence and Fluorescent-Antibody Techniques", Tortora, et al., Microbiology—An Introduction, Fourth Edition, 1992, pp. 461-463.
World Health Organization, "CDC protocol of realtime RTPCR for influenza A (H1N1)," Apr. 28, 2009.
Wiecek, A., "Pocket PCR: The Whole Chain Reaction in His Hand," Biotechniques.com, Oct. 26, 2010.
Danila Valmori et al. "Use of human universally antigenic tetanus toxin T cell epitopes as carriers for human vaccination" Journal of Immunology Jul. 15, 1992.
PCT Search Report for PCT/US2008/074521 dated Feb. 13, 2009.
PCT Written Opinion for PCT/US2008/074521 dated May 3, 2009.
PCT Search Report for PCT/US10/43546 dated Nov. 16, 2010.
PCT Search Report for PCT/US10/31716 dated Jul. 28, 2010.
PCT Written Opinion for PCT/US10/31716 dated Oct. 25, 2011.

De Folette et al. Vaccine 2006, Jun. 12, vol. 24, No. 44-46, pp. 6597-6601.
Galarza et al. Viral Immunity 2005, vol. 18, No. 2, pp. 365-372.
Arend et al. Infection and Immunity, 2000, vol. 68, No. 6, pp. 3314-3321.
Geysen, et al., "Use of Peptide Synthesis to Probe Viral Antigens for Epitopes to a Resolution of a Single Amino Acid," Proc. Natl. Acad. Sci., 81, pp. 3998-4002 (1984).
Valmori, et al., "Use of Human Universally Antigenic Tetanus Toxin T Cell Epitopes as Carriers for Human Vaccination," J. of Immunol., 149(2), pp. 717-721 (1992).
Tolman, et al., "Cyclic V3-Loop Related HIV-1 Conjugate Vaccines," Int. J. Peptide Protein Res., 41, pp. 455-466 (1993).
Conley, et al., "Immunogenicity of Synthetic HIV-1 Gp120 V3-Loop Peptide-Conjugate Immunogens," Vaccine, 12(5), pp. 445-451 (1994).
Schneider, et al., "Induction of CD8+T Cells Using Heterologous Prime-Boost Immunisation Strategies," Immunol. Rev., 170, pp. 29-38 (1999).
Tanghe, et al., "Improved Immunogenicity and Protective Efficacy of a Tuberculosis DNA Vaccine Encoding Ag85 by Protein Boosting," Infect. and Immun., 69(5), pp. 3041-3047 (2001).
Gonzalo, et al., "A Heterologous Prime-Boost Regime Using DNA and Recombinant Vaccinia Virus Expressing the Leishmania infantum P36/LACK Antigen Protects BALB/c Mice from Cutaneous Leishmaniasis," Vaccine, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," J. of Virol., 76(5) pp. 2150-2158 (2002).
Robinson, "New Hope for an AIDS Vaccine," Nat. Rev. Immunol., 2, pp. 239-250 (Apr. 2002).
Lu, et al., "Multiepitope Trojan Antigen Peptide Vaccines for the Induction of Antitumor CTL and Th Immune Responses," J. of Immunol., 172, pp. 4575-4582 (2004).
Westerfield, et al., "Peptides Delivered by Immunostimulating Reconsituted Influenza Virosomes," J. of Peptide Sci., 11(11), pp. 707-712 (2005).
Gerhard, et al., "Prospects for Universal Influenza Virus," Emerging Infectious Diseases, 12(4), pp. 569-574 (Apr. 2006).
Luo, "Structural Biology: Antiviral Drugs Fit for a Purpose," Nature, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Idenitifed in Silico Induce Protective Immunity Against Multiple Influeza Serotypes," Eur. J. of Immunol., 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," J. of Virol., 82(1), pp. 435-450 (Jan. 2008).
Chien et al. J. Clin. Microbiol. 1999, vol. 37, No. 5, 1393-1397.
Ishioka et al. J. Immunol. vol. 162, pp. 3915-3925.
Lederman et al. Molecular Immunology 1991, vol. 28, No. 11, pp. 1171-1181.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
Morré, et al., "RNA Amplification by Nucleic Acid Sequence-Based Amplification with an Internal Standard Enables Reliable Detection of Chlamydia trachomatis in Cervical Scrapings and Urine Samples," J. of Clinical Microbiol., 34(12): 3108-3114 (1996).
Rosenstraus, et al., "An Internal Control for Routine Diagnostic PCR: Design, Properties, and Effect on Clinical Performance," J. of Clinical Microbiol., 36(1): 191-197 (1998).
Daum, et al., Abstract and Poster—"Development of a Real Time Reverse-Transcription PCR (RRT-PCR) Assay for Detection of Influenza A H1N1 2009 From Clinical Respiratory Specimens," Pediatric Infectious Disease Conference ESPID, Nice, France, May 5-8, 2009.
Daum, et al., Abstract—"A Molecular Transport Medium (MTM) for Pathogen Inactivation, Ambient Transport and Preservation of RNA From Clinical Samples," ICAAC, Boston, MA, Sep. 12-15, 2010.
U.S. Appl. No. 12/426,890, filed Apr. 20, 2009, Fischer et al.

U.S. Appl. No. 12/510,968, filed Jul. 28, 2009, Fischer et al.

Chomezynski, P. And Sacchi, N., "Single-Step Method of RNA Isolation by Acid Guanidinium Thiocyanate-Phenol-Chloroform Extraction," *Anal. Biochem.*, 162:156-9 (1987).

Tortora, et al., "Tools of Biochemistry 5A—Ways to Isolate and Purify Proteins and Other Macromolecules," *Microbiology—An Introduction*, pp. 152-155, 4th Ed., The Benjamin/Cummings Publishing Company, Inc., United States (1992).

Ramanujam, R. et al., "Room-Temperature-Stable PCR Reagents," Cold Spring Harbor Laboratory Press, *PCR Methods and Appl.*, 3:75-76 (1993).

Wolff, C. et al, "Single-Tube Nested PCR With Room-Temperature-Stable Reagents," Cold Spring Harbor Laboratory Press, *PCR Methods and Appl.*, 4:376-79 (1995).

Matthews, et al., "Immunofluorescence and Fluorescent Antibody Techniques," *Biochemistry*, pp. 461-463, 2nd Ed., The Benjamin/Cummings Publishing Company, Inc., United States (1996).

Schultz, C.L. et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," *Am. J. Clin. Pathol.*, 111(6):748-52 (1999).

Daum, L.T. et al., "Genetic and Antigenetic Analysis of the First A/New Caledonia/20/99-Like H1N1 Influenza Isolates Reported in the Americas," *Emerg. Infect. Dis.*, 8(4):408-12 (Apr. 2002).

De Moreau de Gerbehaye. A.I. et al., "Stable Hepatitis C Virus RNA Detection by RT-PCR During Four Days Storage," BioMed Central, *BMC Infectious Diseases*, 2:22 (2002).

Daum, L.T. et al., "A Rapid. Single-Step Multiplex Reverse Transcription-PCR Assay for the Detection of Human H1N1, H3N2 and B Influenza Viruses," *J. of Clinic. Virol.*, 25(3): 345-50 (2002).

Spackman, E. et al., "Development of a Real-Time Reverse Transcriptase PCR Assay for Type A Influenza Virus and the Avian H5 and H7 Hemagglutinin Subtypes," *J. of Clinic. Microbiol.*, 40(9): 3256-60 (2002).

Blacksell, S.D. et al., "The Effect of Sample Degradation and RNA Stabilization on Classical Swine Fever Virus RT-PCR and ELISA methods," *J. Virol. Methods*, 118(1):33-7 (2004).

Fouchier, R.A.M. et al., "Characterization of a Novel Influenza A Virus Hemagglutinin Subtype (H16) Obtained From Black-Headed Gulls," *J. of Virol.*, 79(5):2814-22 (Mar. 2005).

Pheng, O.C. et al., "Temperature Related Storage Evaluation of an RT-PCR Test Kit For The Detection of Dengue Infection in Mosquitoes," (Research Note), *Tropical Biomedicine*, 22(1):73-6 (2005).

"USB Taq PCR Master Mix in qPCR," USB Corporation, *Tech Tips*, 207 (2005).

Bright, R.A., et al., "Adamantane Resistance Among Influenza A Viruses Isolated Early During the 2005-2006 Influenza Season in the United States," *JAMA*, 295(8):891-4 (Feb. 22, 2006).

Das, A. et al., "Development of an Internal Positive Control for Rapid Diagnosis of Avian Influenza Virus Infections by Real-Time Reverse Transcription-PCR with Lyophilized Reagents," *J. of Clinic. Microbiol.*, 44(9):3065-73 (Sep. 2006).

Daum. L.T., et al., "Molecular Analysis of Isolates From Influenza B Outbreaks in the U.S. and Nepal, 2005," *Arch. Of Virol.*, 151:1863-1874 (2006).

Lin, B. et al., "Broad-Spectrum Respiratory Tract Pathogen Identification Using Resequencing DNA Microarrays," *Genome Res.*, 16(4): 527-35 (2006).

Mohany, J. et al., "Multiplex RT-PCR for Detecting Nineteen Respiratory Viruses," *J. of Clinic. Virol.*, 36: S9 (2006).

Daum, L.T. et al., "Real-Time RT-PCR Assays For Type and Subtype Detection Of Influenza A and B Viruses," *Influenza & Other Resp. Viruses*, 1(4): 167-75 (2007).

"PCR-Ready Clear Supreme™," Syntezza Bioscience Ltd., available at http://www.syntezza.com/egt/PCR-Ready_Clear_Supreme.pdf (2006).

Wang, Z., et al "Identifying Influenza Viruses with Resequencing Microarrays," *Emerg. Infect. Dis.* 12(4):638-46 (2006).

"TechNotes Newsletter," *Applied Biosystems*, 14(4):1-37 (2007).

Daum, L.T., et al., "Poster—A Rapid, Simplified Collection-to-Detection System for Typing and Subtyping Influenza Viruses Using Real-Time RT-PCR and Culture," *American Society for Microbiology (ASM) Conference on Emerging Technologies of Medical Importance for the Diagnosis of Infectious Diseases and the Detection of Pathogenic Microbes*, Beijing, China, (2008).

Daum, L.T., et al., "Abstract—Quantitation of Influenza A Virus From Nasal and Lung Tissue of Cotton Rats Using Real-Time RT-PCR and Culture," 26th *Annual Meeting of the European Society for Pediatric Infectious Diseases*, Graz, Austria, (2008).

Daum, L.T., et al., "Abstract—Development and Clinical Evaluation of Rapid Real-Time RT-PCR Assays for Detection of Influenza A and B Viruses," 26th *Annual Meeting of the European Society for Pediatric Infectious Diseases*, Graz, Austria, (2008).

Daum, L.T., et al., "Poster—A Novel Specimen Collection Solution for Molecular Diagnostic Applications." *The Pediatric Academic Societies* (*PAS*) *Annual Meeting*, Honolulu, HI (2008).

Daum, L.T., et al., "Poster—Real-Time RT-PCR Detection of Influenza A Virus in Asymptomatic Culture-Negative Cotton Rats," *The Pediatric Academic Societies* (*PAS*) *Annual Meeting*, Honolulu, HI (2008).

Daum, L.T., et al., "Real-Time RT-PCR Detection of Influenza Virus Within Symptomatic and Asymptomatic Family Members," *The 48th Annual IDSA/ICAAC*, Washington D.C. (2008).

European Patent Office, "PCT Notification of Transmittal of the International Search Report and The Written Opinion of the International Searching Authority or the Declaration, PCT International Search Report, PCT Written Opinion of the International Searching Authority—Application No. PCT/US2007/078025," Nov. 13, 2008, 10 pages.

"Abstracts—27th Annual Meeting of the European Society for Paediatric Infectious Disease, Brussels, Belgium, Jun. 9-13, 2009," *The Ped. Infect. Dis. J.*, 28(6):e1, e75, e202, e229 (Jun. 2009).

European Patent Office, "PCT Notification of Transmittal of the International Search Report and The Written Opinion of the International Searching Authority or the Declaration, PCT International Search Report, PCT Written Opinion of the International Searching Authority—Application No. PCT/US2008/078499," Aug. 4, 2009, 13 pages.

Borns, M. et al. "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Stratagene.html (last visited Aug, 24. 2009).

"KOD Hot Start DNA Polymerase," Novagen, available at http://www.emdbiosciences.com/Products/ProductDisplay.asp?catno=71086 (last visited Aug. 24, 2009).

"R.A.P.I.D® System," Idaho Technology Inc., available at http://www.idahotech.com/RAPID/Rapid-Water.html (last visited Aug. 24, 2009).

"AgPath-ID™ One-Step RT-PCR Kit," Applied Biosystems, available at http://www.abion.com/techlib/prot/bp_1005.pdf (last visited Aug. 24, 2009).

"PCR Optimization: Reaction Conditions and Components," Applied Biosystems, Part No. 4371091, Revision C, pp. 1-6 available at http://www3.appliedbiosystems.com/cms/groups/mcb_marketing/documents/generaldocuments/cms_042520.pdf (last visited Aug. 24, 2009).

"Single Tube PCR Kit Manual," Takara Bio Inc., Cat. #RR021, V.02.09, pp. 1-6 available at http://www.takara-bio.us/files/manuals/TAK_RR021_TM.pdf (last visited Aug. 24, 2009).

"Luminex Confirms Effectiveness of xTAG® Respiratory Viral Panel for Swine Flu Surveillance," *Medical News Today*, available at http://www.medicalnewstoday.com/printerfriendlynews.php?newsid=148498 (May 1, 2009).

"Luminex Receives FDA Clearance for an Update to the xTAG® Respiratory Viral Panel Package Insert Package Insert to Include Data from Two New Publications on 2009 Influenza A/H1N1," available at http://phx.corporate-ir.net/phoenix.zhtml?c=79403&p=irol-newsArticle&ID=1307416&highlight=(Jul. 14, 2009).

Luke T. Daum et al., "Detection and Molecular Characterization of Clinical Influenza A and B Viruses from Original Nasal Wash Specimens Preserved in PrimeStore™," (2008).

Luke T. Daum et al., "Portugal Meeting Poster (Introduction, Materials and Methods, Results, Discussion)," (2008).

A. E. Krafft at al., "Evaluation of PCR Testing of Ethanol-Fixed Nasal Swab Specimens as an Augmented Surveillance Strategy for Influenza Virus and Adenovirus Identification," *Journal of Clinical Microbiology*, vol. 43(4), Apr. 2005, pp. 1768-1775.

Linda C. Canas, "Clinical Laboratory: Selection, Collection, and Transport of Specimens for Viral Cultures," Department of the Air Force, Air Force Institute of Operational Health (AFIOH), Epidemiological Surveillance Division, SDE 01 44/5001, *Virology Procedure Manual*, Sep. 2005, pp. 1-8.

"Collecting, preserving and shipping specimens for the diagnosis of avian influenza A(H5N1) virus infection: Guide for field operations," WHO/CDS/EPR/ARO/2006.1, Oct. 2006.

Jamie A. Blow et al., "Viral nucleic acid stabilization by RNA extraction reagent," *Journal of Virological Methods*, 150 (2008), Feb. 4, 2008, pp. 41-44.

CA Office action for PCT/US08/78499, dated Mar. 29, 2012.
CA Office action for PCT/US2007/078025, dated Jan. 4, 2011.
EPO Exam Report for PCT/US2007/078025, dated Dec. 30, 2011.
EPO Exam Report for PCT/US2007/078025, dated Aug. 26, 2010.
EPO Exam Report for PCT/US2007/078025, dated Jul. 6, 2009.
EPO Exam Report for PCT/US2007/078025, dated May 18, 2009.
AU Exam Report for PCT/US2007/078025, dated Nov. 19, 2010.
IL Exam Report for PCT/US2007/078025, dated Mar. 16, 2011.
NZ Exam Report for PCT/US2007/078025, dated Jul. 7, 2010.
Israel Office Action of Jul. 19, 2012.

EPO Supplementary Search Report for PCT/US10/31761, dated Jul. 13, 2012.
CA Office Action for PCT/US2008/078499, dated Mar. 29, 2012.
PCT Written Opinion for PCT/US2008/078499, dated Jul. 4, 2010.
"Monolithic Silica Extraction Tips for Sample Preparation," CP-Analytica, available at http://cp-analytica (last visited Oct. 25, 2010).
Barnard, et al., "Suitability of new chlamydia transport medium for transport of herpes simplex virus," J. of Clin. Microbiol., 24(5): 692-695 (1986).

Eroglu, et al., "Successful cyropreservation of mouse oocytes by using low concentrations of trehalose and dimethylsylfoxide," Biol. of Rep. 80:70-78 (2009).

Gelmi, et al., "Bacertial survival in different transport media," European Congress of Clinical Microbiology and Infectious Diseases (ECCMID), May 28-31, 2000 (poster).

Higashiyama, T., "Novel functions and applications of terhalose," Pure Appl. Chem. 74(7): 1263-1269.

H1N1 RTPCR Primer/Probe Sets, Intergrated DNA Technologies—H1N1, available at http://www.idtdna.com/catalog/h1n1/pagel.aspx.

Johnson, F.B., "Transport of viral specimens," Clin. Microbiol. Rev. 3(2): 120-131 (1990).

Sponseller, et al., "Influenza A pandemic (H1N1) 2009 virus infection in domestic cat," Emerg. Infect. Dis. (e-publication) (2010).

PCT Patentability Report for PCT/US2010/043546, dated Jan. 31, 2012.

PCT Search Report and Patentability Report for PCT/US2008/074521, dated Mar. 2, 2010.

| | Qiagen Viral Mini | | Ambion RNaqueous Mini | | Ambion AI/NCD MagMax | |
|---|---|---|---|---|---|---|
| | One Step− | One-Step+ | One Step− | One-Step+ | One Step− | One-Step+ |
| Real-Time CT Value | 19.25 | 19.08 | 32.83* | 30.39* | 23.95 | 21.26 |
| Viral Copies Detected | 4.7 X $10^9$ | 5.5 X $10^9$ | 2.5 X $10^5$ | 6.2 X $10^{5*}$ | 1.12 X $10^{10}$ | 2.10 X $10^{10}$ |

FIG.2

| Sample | Day 1 | Day 3 | Day 4 |
|---|---|---|---|
| One-Step Solution | 23.97 | 21.37 | 31.38 |
| RNA Storage Solution (Ambion) | 25.35 | 32.70 | 32.20 |
| Water | 24.39 | 32.17 | 32.27 |

|  | Blood Tube | | | |
|---|---|---|---|---|
|  | EDTA | NaCitrate | LiHeparin | NaHeparin |
| PrimeStore™ | 33.7804 | 31.9677 | 32.5538 | 33.118 |
|  | 34.7485 | 32.0509 | 32.8927 | 32.984 |
| AVG: | 34.26445 | 32.0093 | 32.72325 | 33.051 |
| Qiagen | 35.3054 | 33.4051 | 34.4903 | 34.6428 |
|  | 34.7485 | 33.4051 | 35.0378 | 35.3937 |
| AVG: | 35.02695 | 33.4051 | 34.76405 | 35.01825 |

FIG. 14B

| PrimeStore™–Blood Extraction | |  |
|---|---|---|
| 1pg | 0.1pg | |
| 32.7715 | 36.434 | |
| 33.2488 | 37.0442 | |
| 33.01015 | 36.7391 | AVG |
| 0.337502067 | 0.431476558 | STDEV |

| Qiagen–Blood Extraction | | |
|---|---|---|
| 1pg | 0.1pg | |
| 35.8461 | 37.5771 | |
| 37.01 | 38.1878 | |
| 36.42805 | 37.88245 | AVG |
| 0.823001583 | 0.431830111 | STDEV |

FIG. 14C

BIOLOGICAL SPECIMEN COLLECTION AND TRANSPORT SYSTEM AND METHODS OF USE

CROSS-REFERENCE TO RELATED APPLICATIONS

The present application is a continuation of U.S. application Ser. No. 12/243,949, Oct. 1, 1998 now U.S. Pat. No. 8,084,443 and claims the benefit of U.S. Provisional Application No. 60/976,728, filed Oct. 1, 2007, the entire contents of which is specifically incorporated herein in its entirety by express reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

FIELD OF THE INVENTION

The invention relates to aqueous compositions for collection, transport, and storage of a biological specimen containing a population of nucleic acids in a single reaction vessel, which can then be purified and/or analyzed using conventional molecular biology methods. In particular, the invention is directed to a one-step composition that a) inactivates viruses or microbes in the sample, b) lyses the biological cells or tissues to free the nucleic acids from cellular debris and extraneous biomolecules, c) protects the nucleic acids from degradation by endonuclease activity, and d) preserves the nucleic acids for subsequent isolation, detection, amplification, and/or molecular analysis. In a particularly advantageous application, all four functions may be achieved in a single composition, and in a single reaction vessel, and the resultant sample may be stored at ambient temperature for extended periods without significant degradation of the polynucleotides contained within the sample.

BACKGROUND OF THE INVENTION

Description of Related Art

In the field of molecular and diagnostic analysis, the ability to keep nucleic acids in a biological sample stable, whether the specimen is taken in a remote field location, a doctor's office or in a laboratory, often determines whether the nucleic acids can be successfully analyzed. Nucleic acids in a biological sample quickly degrade and/or denature at room temperature and must generally be stored under freezing temperatures to remain stable; however, some degree of degradation still occurs over time. This problem is magnified when a specimen is collected at a remote field site, or a significant distance from a doctor's office or laboratory environment, and especially where there may be limited, or no, access to consistent and constant cooler/refrigerator/freezer conditions until the sample is analyzed, such as where access to power (i.e., electricity), or freezer equipment is not constant or is non-existent. The problem is yet further magnified when the desired nucleic acids for downstream analysis include ribonucleic acid (RNA), which is particularly susceptible to degradation, e.g., by endogenous or exogenous endonuclease activity. Specimen transport technology presently available in the art often uses special transport media for biological samples for transport to a laboratory, in particular, packaging that imposes short time, low temperature, and practicality limits.

In addition to concerns regarding specimen stability, often there are additional concerns regarding the reagents that are used to store and/or transport the collected samples. For example, the reagents themselves frequently require cold temperatures or other special care to maintain stability. Due to these stability issues, for example, transport of the reagents to a field site, storage at the field site before use, and transport of the biological specimens and reagents back to a testing site is a primary concern.

Another significant concern when working with biological specimens is the potential inoculation, release, or dissemination of live infectious pathogens or biological agents from the specimen into the environment. Specific protocols currently exist that are employed when handling samples that may be infectious or otherwise pose health or safety risks. If the sample is kept viable and/or biologically intact to preserve its integrity for testing, individuals involved in the collection, transfer, and testing process are potentially exposed to highly dangerous contagions. Additionally, innocent bystanders nearby a field site (or nearby during transport) can be exposed if a release of the contagion occurs. As a result, the required safety measures typically increase the expense and effort required to move such samples from one location to another.

Until recently, clinical laboratory methods for pathogen detection were labor-intensive, expensive processes that required highly knowledgeable and expert scientists with specific experience. The majority of clinical diagnostic laboratories employed the use of traditional culturing methods that typically require 3 to 7 days for a viral culture—and even longer for some other bacterial targets. Furthermore, traditional culturing requires collection, transport, and laboratory propagation and handling of potentially infectious biological agents such as Ebola, avian influenza, severe acute respiratory syndrome (SARS), etc.

The field of clinical molecular diagnostics changed drastically with the advent of polymerase chain reaction (PCR) in the mid eighties, however, and shortly thereafter with real-time PCR in the mid 90's. Real-time PCR (and RT-PCR) can deliver results in hours, and the majority of modern diagnostic laboratories are transitioning away from traditional culture, and into nucleic-acid-based detection platforms, such as real-time PCR. Recent improvements in detection chemistries, such as new and improved reporting/quenching fluors, minor groove binders (MGB), and stabilized amplification reagents have paved the way for more sensitive and specific pathogen detection assays that have been proven more timely, robust, and economical than antiquated culturing methods. Advances in other nucleic acid detection strategies (in addition to real-time PCR) such as transcription-mediated amplification, ligase chain reaction (LCR), microarrays, and pathogen gene chips, have also contributed to a transition from culture vials in the clinical laboratory.

Several commercial companies (e.g., Qiagen, Roche, and bioMérieux) have developed automated nucleic acid extraction instruments, and have attempted to automate the parts of the multi-part process from sample isolation to molecular analysis. For example, the Tigris DTS® (Gen-Probe, San Diego, Calif., USA) automates the entire detection process, and in late 2004 was FDA approved for use with Gen-Probe's APTIMA COMBO 2® assay, an FDA-approved amplified nucleic acid test (NAT) for simultaneously detecting *Chlamydia trachomatis* and *Neisseria gonorrhoeae*.

Accordingly, there is a need in the art for a safe collection, storage and transport system that maintains the integrity of the nucleic acids of even a dangerous biological specimen, typically for further molecular analysis or diagnostic testing, without the need for freezing the collected biological specimen, the collection reagents, or the collected sample in the reagents, without posing a risk to workers or innocent bystanders, and allowing for the use of less expensive and more convenient transportation methods or complicated shipping precautions.

BRIEF SUMMARY OF THE INVENTION

The present invention encompasses new and useful compositions, as well as methods of making and employing them, that may advantageously improve conventional collection, lysis, transport and storage methods for the preparation of nucleic acids from one or more biological sources. Accordingly, the present invention advantageously can provide a collection and preservation formulation to inactivate and lyse a biological specimen containing nucleic acids, and preserve nucleic acids (RNA/DNA) within the biological specimen, preferably all in a single reaction vessel, such that the integrity of the nucleic acids is at least substantially maintained, and preferably entirely maintained, so that a portion of the nucleic acids are readily available for molecular diagnostic analysis.

An additional advantage of the present invention is that the formulation can enable the separated or released nucleic acids to remain at least substantially stable, without requiring consistent and constant cooler temperatures, such as refrigeration or freezing.

The one-step formulations disclosed herein accomplish the following main functions: inactivation or killing of pathogens within the sample; lysis of cells and separation or release of nucleic acids from the cells; inactivation of endogenous or exogenous nucleases and other cellular enzymes to prevent degradation of the nucleic acids present in the sample; and facilitation of collection and handling of the sample at ambient temperatures, stabilization of the nucleic acids during subsequent transport and storage of the sample, and preservation/maintenance of the integrity of one or more polynucleotides contained with the liberated nucleic acids.

The ability to achieve all of these desirable functions in a single-step formulation, preferably in a single reaction zone or reaction vessel, is a particularly marked advantage over that presently available. Presently existing technologies do not include a single-step composition that provides for inactivation of biological components containing nucleic acids, release of nucleic acids through lysis of cells and separation or release of nucleic acids, and maintenance of the integrity of the nucleic acids. Without being bound by theory, this is in part believed to be because the process of killing the biological organism present in a sample typically results in release and activation of enzymes that degrade proteins and nucleic acids. Enzymatic degradation leads to sample destruction, which prevents analysis. The present invention, however, stabilizes and preserves the integrity of nucleic acids present in the specimen for diagnostic testing.

The one-step formulations of the present invention allow for preferably simultaneous inactivation of biological components containing nucleic acids, lysis and separation or release of nucleic acids, stabilization, and preservation. In one embodiment, some or all of the inactivation, lysis and separation or release, stabilization, and preservation, are sequential. In a preferred embodiment, however, a majority or preferably all of these functions occur simultaneously. In all embodiments, the one-step formulation is combined with the sample to initiate these functions. This is in contrast to previous technology in which inactivation did not necessarily occur, and lysis, stabilization, and preservation occurred in a succession of separate steps, each step typically using one or more distinct reagents and protocols that were separately added.

The sequential format of prior procedures was needed to minimize errors, avoid reagent incompatibility, and provide stepwise control of results. The present invention provides all these benefits and adds the further benefits of maintaining the integrity of the nucleic acids, rendering them ready for extraction and purification, thereby improving their ultimate yield. The one-step formulation's preferably simultaneous inactivation of biological components containing nucleic acids, lysis and release of nucleic acids from cellular debris, stabilization, and preservation of nucleic acids reduces the chance for degradation of the RNA/DNA in the sample that may occur during lysis, or after lysis and before stabilization, which contributes to improved yield of the nucleic acids that are eventually extracted. An improved yield can lead to superior test results.

In one embodiment, the invention provides a composition that includes: a) one or more chaotropes (each preferably present in the composition an amount from about 0.5 M to about 6 M); b) one or more detergents (each preferably present in the composition an amount from about 0.1% to about 1%); c) one or more chelators (each preferably present in the composition in an amount from about 0.01 mM to about 1 mM); d) one or more reducing agents (each preferably present in the composition in an amount from about 0.05 M to about 0.3 M); and e) one or more defoaming agents (each preferably present in the composition in an amount from about 0.0001% to about 0.3%).

Exemplary chaotropes include, without limitation, guanidine thiocyanate (GuSCN), guanidine hydrochloride (GuHCl), guanidine isothionate, potassium thiocyanate (KSCN), sodium iodide, sodium perchlorate, urea, or any combination thereof. Descriptions of additional exemplary chaotropes and chaotropic salts can be found in, inter alia, U.S. Pat. No. 5,234,809 (specifically incorporated herein in its entirety by express reference thereto).

Exemplary detergents include, without limitation, sodium dodecyl sulfate (SDS), lithium dodecyl sulfate (LDS), sodium taurodeoxycholate (NaTDC), sodium taurocholate (NaTC), sodium glycocholate (NaGC), sodium deoxycholate (NaDC), sodium cholate, sodium alkylbenzene sulfonate (NaABS), N-lauroyl sarcosine (NLS), salts of carboxylic acids (i.e., soaps), salts of sulfonic acids, salts of sulfuric acid, phosphoric and polyphosphoric acid esters, alkylphosphates, monoalkyl phosphate (MAP), and salts of perfluorocarboxylic acids, anionic detergents including those described in U.S. Pat. No. 5,691,299 (specifically incorporated herein in its entirety by express reference thereto), or any combination thereof.

Exemplary reducing agents include, without limitation, 2-mercaptoethanol β-ME), tris(2-carboxyethyl) phosphine (TCEP), dithiothreitol (DTT), formamide, dimethylsulfoxide (DMSO), or any combination thereof. In a preferred embodiment, the reducing agent includes or is TCEP.

Exemplary chelators include, without limitation, ethylene glycol tetraacetic acid (EGTA), hydroxyethylethylenediaminetriacetic acid (HEDTA), diethylene triamine pentaacetic acid (DTPA), N,N-bis(carboxymethyl)glycine (NTA), ethylenediaminetetraacetic (EDTA), citrate anhydrous, sodium citrate, calcium citrate, ammonium citrate, ammonium bicitrate, citric acid, diammonium citrate, potassium citrate, magnesium citrate, ferric ammonium citrate, lithium citrate, or any combination thereof. In preferred embodiments, the chelator includes EDTA, a citrate, or a combination thereof. In a more preferred embodiment, the chelator includes EDT.

The compositions of the invention can further include a defoaming agent to prevent the formation of bubbles that typically result from the presence of detergents in the formulation. Defoaming agents facilitate pipetting and handling of the disclosed compositions. Exemplary surfactants/defoaming agents include, without limitation, cocoamidopropyl hydroxysultaine, alkylaminopropionic acids, imidazoline carboxylates, betaines, sulfobetaines, sultaines, alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, alkylpolyglycosidases, silicone polymers such as Antifoam A®, or polysorbates such as Tween®, or any combination thereof. In a preferred embodiment, a defoaming agent includes a silicone polymer.

Optionally, the compositions of the invention may further include one or more buffers (each preferably present in the final composition in an amount from about 1 mM to about 1 M). Exemplary buffers include, without limitation, tris(hydroxymethyl)aminomethane (Tris), citrate, 2-(N-morpholino)ethanesulfonic acid (MES), N,N-Bis(2-hydroxyethyl)-2-aminoethanesulfonic Acid (BES), 1,3-bis(tris(hydroxymethyl)methylamino)propane (Bis-Tris), 4-(2-hydroxyethyl)-1-piperazineethanesulfonic acid (HEPES), 3-(N-morpholino)propanesulfonic acid (MOPS), N,N-bis(2-hydroxyethyl)glycine (Bicine), N-[tris(hydroxymethyl)methyl]glycine (Tricine), N-2-acetamido-2-iminodiacetic acid (ADA), N-(2-Acetamido)-2-aminoethanesulfonic acid (ACES), piperazine-1,4-bis(2-ethanesulfonic acid) (PIPES), bicarbonate, phosphate, or any combination thereof. In a preferred embodiment, the buffer includes a citrate.

The inclusion of one or more of such optional but preferred buffers is desirable to control the pH of the formulations, since it has been found that nucleic acid extraction is optimal in a pH range of about 5 to 7. Preferably, the one or more buffers employed in the disclosed compositions are chosen to provide a significant buffering capacity in the range from a pH of about 6 to a pH of about 8, more preferably within a pH range of about 6 to about 7, and more preferably still, within a pH range of about 6.2 to about 6.8. In exemplary embodiments, the pH of PrimeStore™ Solutions (also referred to herein as "PSS") is preferably about 6.7±0.25.

The compositions of the invention may also further optionally include one or more short-chain (preferably from 1- to 6-carbon [i.e., $C_1$-$C_6$] alcohols) alkanols (each preferably present in the composition in an amount from about 1% to about 25%, although higher percentages of the alcohols may be employed if desired). Exemplary short-chain alkanols include linear and branched-chain alcohols, such as, without limitation, methanol, ethanol, propanol, butanol, pentanol, hexanol, or any combination thereof.

The compositions of the invention may also further optionally include one or more additional compounds or reagents including, without limitation, betaine, bovine serum albumin, and osmolytes such as trehalose, sorbitol, and the like.

In certain embodiments, the addition of nucleic acids (e.g., RNA and/or DNA) is contemplated to be beneficial for a variety of purposes and applications of the disclosed methods: a) as a "carrier" (The addition of small amounts of supplemental RNA/DNA has been previously been shown to augment/increase the overall yield of samples/specimens, particularly original specimens that may contain low amounts of target, i.e., cells, viruses, bacteria); b) as an internal positive control for downstream molecular processes and to track or monitor the fidelity of the nucleic acid preparation from sample collection to detection; and c) for comparison to a 'calibrator' for downstream quantitative analysis, e.g., qRT-PCR and the like. In such embodiments, one or more known or "control" nucleic acids could be added to the compositions in a final concentration of from about 1 pg to about 1 μg.

Preferably, the compositions of the invention provide sufficient buffering capacity to adequately stabilize the populations of polynucleotides obtained from a sample, and will, most preferably, be buffered to a pH of about 6.4 to 6.9 during formulation, and will maintain the isolated populations of polynucleotides in a similar pH range when the sample is contacted with the storage/collection formulations described herein.

Preferably, the collected samples will include one or more populations of nucleic acids that are isolated from a biological sample, specimen, or source, including, for example, RNAs and DNAs.

The compositions of the present invention will typically at least substantially inactivate, and preferably entirely inactivate, any endogenous or exogenous RNAses or DNAses present in the sample, such that the nucleic acids of the sample are substantially free of any degradation, and preferably do not degrade, or lose integrity, during the collection, lysis, storage, and transport of the sample for subsequent in vitro or in vivo analyses.

Exemplary formulations of the invention include a one-step collection solution that lyses, stabilizes, and preserves the integrity of nucleic acids prepared from a biological sample for subsequent RNA and/or DNA analysis.

The disclosed compositions were developed and optimized, inter alia: 1) to facilitate preparation of high-quality nucleic acids from clinical or environmental specimens, 2) to inactivate, kill, or otherwise neutralize potentially infectious pathogens in a biological sample to facilitate safe handling and transport of the collected specimens, and 3) to stabilize released (i.e., 'naked') DNA/RNA for prolonged periods without hydrolysis or nuclease degradation of the released nucleic acids.

The compositions described herein are ideal for clinical, field and deployment use, or for high volume sample collection/extraction. Specimens collected in one or more of the disclosed compositions are biologically inactivated, and may be safely shipped, typically even without refrigeration or dry ice.

Exemplary formulations of the storage/transport/collection compositions of the invention are described in the examples herein, and include, without limitation, a composition that includes about 4 M of a chaotrope (such as guanidine thiocyanate, guanidine hydrochloride, guanidine isocyanate, or any combination thereof), about 10 mM to 30 mM of a chelator (such as EGTA, HEDTA, DTPA, NTA, EDTA, citrate anhydrous, sodium citrate, calcium citrate, ammonium citrate, ammonium bicitrate, citric acid, diammonium citrate, ferric ammonium citrate, lithium citrate, or any combination thereof), about 0.25% of a detergent (such as SDS, LDS, NaTDC, NaTC, NaGC, NaDC, sodium cholate, NaABS, NLS, or any salt or combination thereof), about 0.1 M of a reducing agent (such as β-ME, DTT, DMSO, formamide, TCEP, or any combination thereof), and about 0.1% of a surfactant/defoaming agent (such as a silicone polymer [e.g., Antifoam A®] or a polysorbate [e.g., Tween®], or any combination thereof).

Additional exemplary formulations of the specimen collection compositions of the invention include, without limitation, a composition that includes about 3 M of a chaotrope (such as guanidine thiocyanate, guanidine hydrochloride, guanidine isocyanate, or any combination thereof), about 1 mM of a reducing agent (such as β-ME, TCEP, formamide, DTT, DMSO, or any combination thereof), about 1 to 10 mM of a chelator (such as EGTA, HEDTA, DTPA, NTA, EDTA, citrate anhydrous, sodium citrate, calcium citrate, ammonium citrate, ammonium bicitrate, citric acid, diammonium citrate, ferric ammonium citrate, lithium citrate, or any combination thereof), about 0.25% of a detergent (such as SDS, LDS, NaTDC, NaTC, NaGC, NaDC, sodium cholate, NaABS, NLS, or any salt or combination thereof), and optionally but preferably about 0.0002% of a defoaming agent (also referred to as an antifoaming agent) (such as a silicone polymer or a polysorbate, or any combination thereof) and about 100 mM of a buffer (such as Tris, MES, BES, Bis-Tris, HEPES, MOPS, bicarbonate, citrate, phosphate, or any combination thereof).

Another exemplary formulation of the disclosed polynucleotide isolation and stabilization compositions include, without limitation, a composition that includes about 1 to about 4 M of a chaotropic agent such as guanidine thiocyanate, guanidine hydrochloride, or guanidine isocyanate; about 0.5 to 100 mM of a chelating agent such as EDTA, or sodium citrate, or both; about 0.1 to about 1% of an anionic detergent such as SDS or N-lauroyl sarcosine, sodium salt; about 0.001 to about 0.0001% of a surfactant or wetting agent such as the silicone polymer, Antifoam A®, e); about 10 to about 500 mM of a buffering agent such as Tris-HCl; and about 10 to about 25% of a short-chain alkanol such as ethanol.

In particular embodiments, the invention provides a composition that includes about 3 M guanidine thiocyanate; about 1 mM TCEP; about 10 mM sodium citrate; about 0.5% N-lauroyl sarcosine, sodium salt; about 0.0002% Antifoam A, about 100 mM Tris-HCl, about 0.1 mM EDTA; and about 23% ethanol.

The invention also provides a method for obtaining a population of polynucleotides from a sample suspected of containing nucleic acids. The method generally involves associating the sample with an amount of one of the disclosed compositions, under conditions effective to obtain a population of polynucleotides from the sample. The invention does not require separation of the population to "obtain" the sample, as later diagnosis may or may not need such separation.

The invention also provides a method of preparing a one-step aqueous formulation of the collection/lysis/transport/storage compositions described herein for the collection of nucleic acids such as RNA and/or DNA. In an overall sense, the method generally involves combining one or more chaotropes and nuclease-free water at a temperature of about 20° C. to 90° C. in a reaction zone; then combining the dissolved one or more chaotropes with one or more reducing agents, one or more chelators, and one or more detergents in the reaction zone to form an intermediate composition; optionally combining a silicone polymer with the intermediate composition in an amount sufficient to minimize foaming during further preparation of the one-step aqueous formulation; combining a sufficient amount of buffer to the intermediate composition to maintain a pH of about 6 to 6.9; optionally combining a second chelating agent to the reaction zone; then increasing the temperature of the second intermediate composition to about 60 to 95° C. for about 1 to 30 minutes and lowering the temperature to ambient conditions; optionally then combining a $C_{1-6}$ alcohol with the contents of the reaction zone; and optionally adjusting the pH to be about 6.4 to 6.9.

In additional embodiments, the invention provides a method for preparing one-step aqueous formulations adapted to obtain a population of polynucleotides from a biological sample that is suspected of containing nucleic acids. This method generally involves at least the steps of:

a) contacting the sample with an amount of the one-step aqueous formulation effective to:
  i) at least substantially kill or inactivate potentially-infectious pathogens in the sample;
  ii) lyse a portion of cells to release RNAs and/or DNAs from the sample; and
  iii) substantially inhibit or prevent the released polynucleotides in the sample from further hydrolysis or enzymatic degradation, modification, or inactivation, so as to obtain the population of polynucleotides from the sample.

Such sample may be of any origin, including, without limitation, a clinical or veterinary sample; an environmental or ecological sample, a forensic or crime scene sample, or such like, and may contain one or more nucleic acids that are of viral, microbial, animal, or plant origin, or any combination thereof.

Preferably, the methods of the invention will include at least contacting the sample with an amount of one or more of the disclosed compositions at a temperature of from 0° C. to about 40° C. (more preferably at a temperature of 4° C. to about 35° C., and still more preferably at a temperature of 10° C. to about 30° C.) for a period of time of at least 24 hrs, more preferably, for a period of time of at least 48 hrs, at least 72 hrs, at least 96 hrs, or longer, without causing substantial deterioration, degradation, enzymatic cleavage, and/or nucleolytic digestion, modification, or processing of the nucleic acids contained within a sample contacted with such a composition.

In certain embodiments, the methods of the invention will include at least contacting the sample with an amount of one or more of the disclosed compositions at a temperature from about 0° C. to about 40° C. (more preferably at a temperature from about 4° C. to about 35° C., still more preferably at a temperature from about 10° C. to about 30° C., and more preferably still at a temperature from about 15° C. to about 25° C.) for a period of time of at least 7 days, more preferably, for a period of time of at least 14 days, at least 21 days, at least 28 days, or even longer without causing significant deterioration, degradation, enzymatic cleavage, and/or nucleolytic processing of the nucleic acids contained within a sample so processed. It should be understood that associating a sample with an inventive composition need only occur for a short time, but to avoid the need for immediate separation of the nucleic acids from the sample and the one-step composition of the invention all the materials may remain in contact for the time periods specified above without any substantial, or without any, degradation of the nucleic acids.

Preferably, the integrity of a population of polynucleotides released from the sample into the composition will be substantially maintained, even when the composition comprising the sample is stored at ambient temperatures, and even for prolonged periods of time, including, without limitation, storage for greater than about 10 days, greater than about 20 days, or even greater than about 30 days or more. Likewise, it is desirable that the integrity of a population of polynucleotides released from the sample into the composition will be substantially maintained, even when the composition comprising the sample is stored at subtropical and tropical temperatures—even for prolonged periods of time, including, without limitation, storage for greater than about 5 days, greater than about 15 days, or even greater than about 25 days or more.

In the practice of the present methods, it is preferable that at least one or more biological cells contained within the sample are substantially lysed to release at least a first population of polynucleotides contained within such cells into the composition. Preferably, the components of the disclosed composition are sufficient to release such a population from the remaining cellular debris (including, without limitation, lipids, proteins, polysaccharides, cellular components, and such like).

It is also desirable in the practice of the present methods that at least one or more exogenous or endogenous nucleases that may be present in, on, or about the sample itself, will be sufficiently inactivated by one or more components of the composition such that the resulting nucleic acids are not destroyed, damaged, or nucleolytically cleaved when the biological cells contained within the sample are substantially lysed to release the population of polynucleotides from the cells. Preferably, one or more components of the disclosed composition are effective to kill, inactivate, or substantially inhibit the biological activity of a DNAse or an RNAse, when such a protein is present in the sample.

It is also desirable in the practice of the present methods that when one or more microbes, viruses, and/or pathogens are present in, on, or about the sample when collected, such microbes, viruses, and/or pathogens will be killed or sufficiently inactivated by one or more components of the composition to facilitate safe handling of the sample by the practitioner. Preferably, one or more components of the disclosed composition are effective to render a pathogenic sample substantially, or preferably entirely, non-pathogenic without the need for adding additional components to the composition. However, in certain applications, it may also be desirable to include one or more additional anti-microbial, anti-viral, or anti-fungal agents to the compositions to render them substantially non-pathogenic, and thus, same for handling by the practitioner.

Preferably, the composition containing the sample is at least sufficiently stable, or is entirely stable, to permit storage of the sample in the composition at ambient temperature or colder at least substantially (or entirely) from the time of collection to the time of analyzing a population of polynucleotides from the sample. As used herein, "ambient temperature" can refer to temperatures of about 18° C. to 25° C., or in some embodiments about 20° C. to 22° C.

In certain embodiments, the composition containing the sample may be stored at a temperature of about 0° C. to about 40° C., more preferably at a temperature of about 4° C. to about 30° C., more preferably, at a temperature of about 10° C. to about 25° C., at least substantially from the time of collection to the time that the polynucleotides obtained from the sample are further isolated, purified, or characterized using one or more conventional molecular biology methodologies.

In certain embodiments, the composition containing the sample suspected of containing nucleic acids will stabilize the nucleic acids to the extent that they either remain at least substantially non-degraded (i.e., at least substantially stable) even upon prolonged storage of the composition at ambient, refrigerator, or sub-zero temperatures. It will be desirable that this stability provides that at least about 70%, at least about 85%, more preferably at least about 90%, more preferably at least about 95%, or even more preferably, at least about 98% of the polynucleotides contained within the stored sample will not be degraded upon prolonged storage of the sample. In certain embodiments, substantially all of the polynucleotides contained within the sample will be stabilized such that the original integrity of the polynucleotides is preserved during the collection, lysis, storage, and transport of the processed sample.

In certain embodiments, the method will preferably provide a population of nucleic acids prepared from a biological sample in which less than about 15% of the polynucleotides contained in the sample will be degraded during the collection, lysis, storage, and transport of the sample after it has been stored in the composition at a temperature of from −20° C. to about 40° C. for a period of at least 24, 48, 72, or 96 hrs or longer after the sample was initially introduced into the composition.

In related embodiments, the method will preferably provide a population of nucleic acids prepared from a biological sample in which less than about 10% of the polynucleotides contained in the sample will be degraded during the collection, lysis, storage, and transport of the sample after it has been stored in the composition at a temperature of from −20° C. to about 40° C. for a period of at least 24, 48, 72, or 96 hrs or longer after the sample was initially introduced into the composition.

Likewise, in some applications of the methodology disclosed herein, use of the disclosed compositions will preferably provide a population of nucleic acids that are prepared from a biological sample, wherein less than about 5% of the polynucleotides contained in the sample will be degraded during the collection, lysis, storage, and transport of the sample after it has been stored in the composition at a temperature from −20° C. to about 40° C. for a period of at least 24, 48, 72, or 96 hrs or longer after the sample was initially introduced into the composition.

In some instances, the population of nucleic acids prepared by the present methods may be maintained with sufficient integrity such that no more than about 1 or 2% of the sample will be degraded even when the composition is stored at a temperature from 0° C. to about 40° C. for periods of several days to several weeks. In fact, the inventors have shown that samples of nucleic acids isolated using the disclosed methods remain at least substantially stable, preferably stable, in their non-degraded form for periods of several weeks to even several months or more, even when the composition containing the nucleic acids is stored at a temperature from 10° C. to about 40° C. In one preferred embodiment, the upper limit on the above-noted temperature ranges is about 37° C. Thus, the term "stable" as used herein may refer to the various embodiments noted above regarding the integrity of the population of nucleic acids after a particular time lapse at a given temperature.

Commercial Formulations and Kits

The present invention also provides kits and sample collection systems utilizing the disclosed compositions and collection/storage/transport solutions described herein. In particular embodiments, such sample collection systems may include a collection device, such as a swab, curette, or culture loop; and a collection vessel, such as a vial test tube, or specimen cup, that contains one or more of the compositions disclosed herein. The collection vessel is preferably releasably openable, such that it can be opened to insert the one-step compositions and closed and packaged, opened to insert the sample and optionally a portion of the collection device and closed for storage and transport, or both. The collection vessel may use any suitable releasably openable mechanism, including without limitation a screw cap, snap top, press-and-turn top, or the like. Such systems may also further optionally include one or more additional reagents, storage devices, transport devices, and/or instructions for obtaining, collecting, lysing, storing, or transporting samples in such systems. In a preferred embodiment, the one-step compositions of the invention may already be disposed in the reaction zone into which the sample may be associated. In such embodiments, the invention requires only a collection device and the collection vessel.

The kit may also include one or more extraction devices to help liberate and separate the nucleic acids to obtain at least substantially pure RNA/DNA to be analyzed.

Kits may also be packaged for commercial distribution, and may further optionally include one or more collection, delivery, transportation, or storage devices for sample or specimen collection, handling, or processing. The container(s) for such kits may typically include at least one vial, test tube, flask, bottle, specimen cup, or other container, into which the composition(s) may be placed, and, preferably, suitably aliquotted for individual specimen collection, transport, and storage. The kit may also include a larger container, such as a case, that includes the containers noted above, along with other equipment, instructions, and the like. The kit may also optionally include one or more additional reagents, buffers, or compounds, and may also further optionally include instructions for use of the kit in the collection of a clinical, diagnostic, environmental, or forensic sample, as well as instructions for the storage and transport of such a sample once placed in one or more of the disclosed compositions. The kit may include, e.g., multiples of about 5 or more of the various collection devices and collection vessels and any other components to be included, so that the kits can be used to collect multiple samples from the same source or different sources.

BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 2 shows the extraction efficiency of PrimeStore™ Solution (ver. 1) compared to commercial kits. Homogenized cotton rat nose(*) challenged with influenza A (H3N2) or a human clinical influenza A (H1N1) samples collected during the 2006-07 season were lysed in the PrimeStore™ Solution or lysed using the respective lyses solution, protocol, and extraction procedure from three commercially available kits: RNaqueous-Micro (Ambion Cat#AM1931), QiaAmp Viral Mini Kit (Qiagen), and AI/NCD MaxMag (Ambion) Kit. Extraction efficiency was evaluated using the ABI 7500 with the comparative CT method. The relative CT scores and viral copies detected were optimal when PrimeStore™ (depicted as the "one-step formulation") was utilized in place of the respective lyses buffer for each commercial kit;

FIG. 3 shows the preservation of naked RNA in PrimeStore™ Solution vs. Ambion RNA Storage Solution. Single-stranded Avian H5 RNA was stored in PrimeStore™ solution, RNA storage solution (Ambion), or water at ambient temperature (22-24° C.) for 96 hours. A total of 5 pg of RNA was extracted using the RNaqueous®-Micro Kit (Ambion, Cat#AM1931) according to manufacturer recommendations and analyzed using real-time RT-PCR on an ABI 7500 (Applied Biosystems). Values are given as cycle thresholds (CT) using the absolute quantification method;

after 7 days. Duplicate reactions were included for each reaction. Real-time RT-PCR Cycle Threshold (CT) values of naked RNA preserved in PrimeStore™ with added nucleases (average CT: 33.51) were detected after 7 days. Template cRNA reactions subjected to nuclease digestion without PrimeStore were completely degraded and similar to NTC reactions.

Figure 8A:
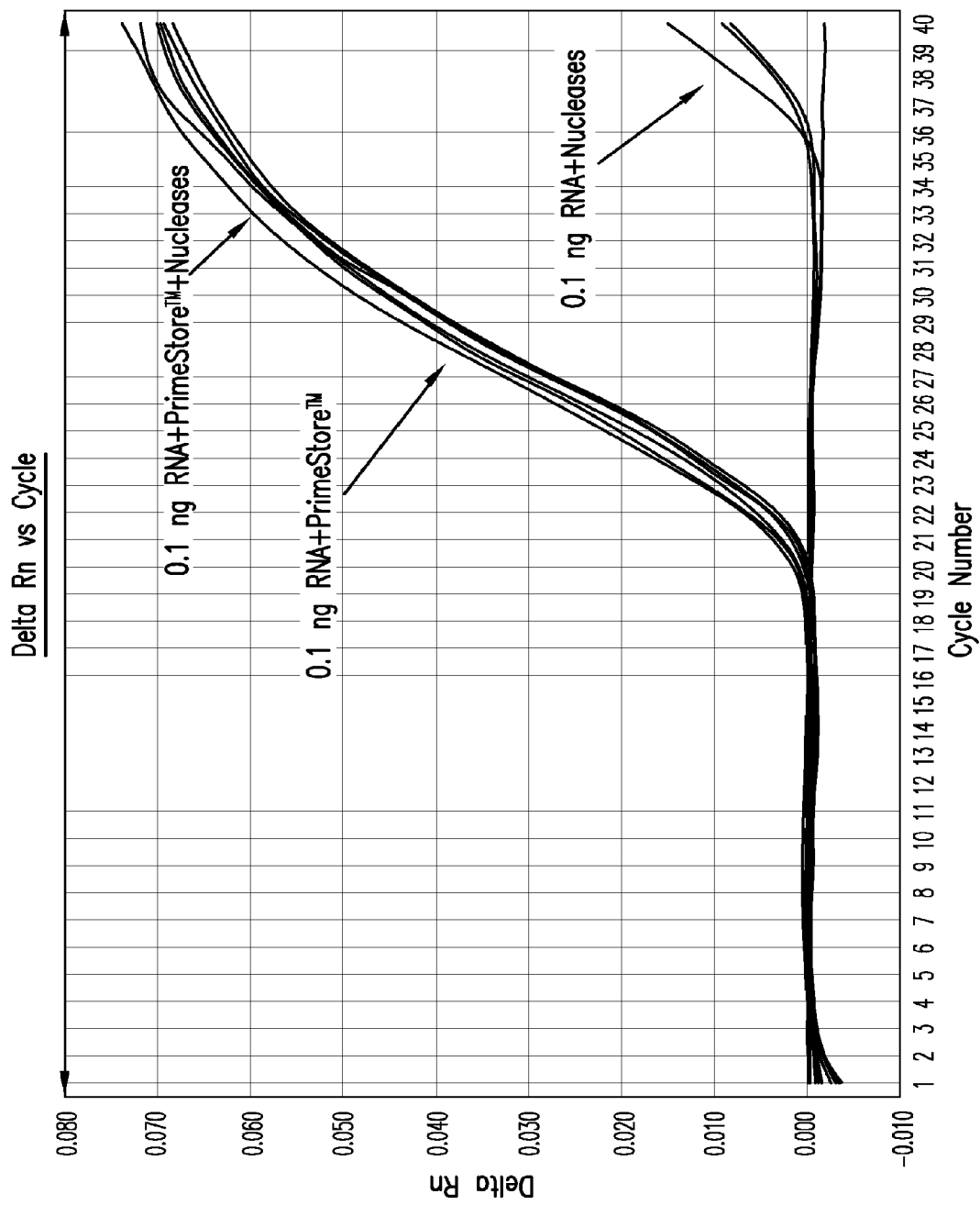
FIG. 8A depicts the real-time RT-PCR analysis of "naked" influenza A avian H5 RNA template preserved in PrimeStore™ Solution after incubation in RNA/DNA nucleases. H5 cRNA (2 ng) was incubated with ribonuclease A and T1, and DNAseI for 1 hour @ 37° C. and extracted using the RNAaqueous®-Micro Kit (Ambion). Triplicate reactions were included for each reaction condition. Real-time RT-PCR Cycle threshold (CT) values of naked RNA preserved in PrimeStore with added nucleases (average CT: 22.88) were similar to an equal quantity of template cRNA control (average CT: 23.70). Template cRNA reactions subjected to nuclease digestion without PrimeStore™ were almost completely degraded (average CT 39.58)
Figure 8B:
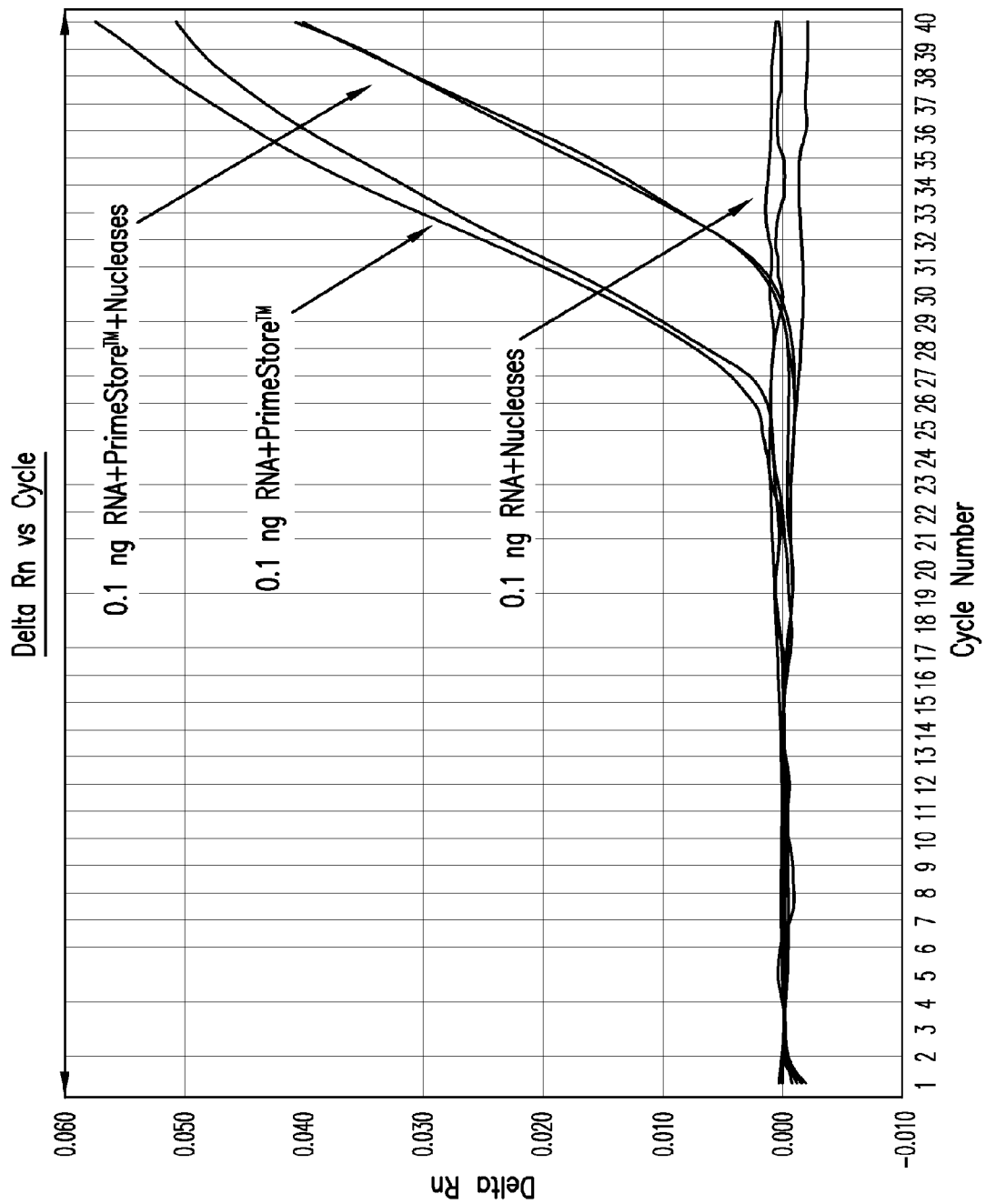
FIG. 8B depicts the real-time RT-PCR analysis and gel electrophoresis of "naked" influenza A avian H5 RNA template preserved in PrimeStore™ Solution after incubation in RNA/DNA nucleases @ 37° C. for 7 days. Two nanograms of H5 cRNA was incubated with RNase A and T1, and DNase I, then extracted using the RNAaqueous®-Micro Kit (Ambion)
Figure 8C:
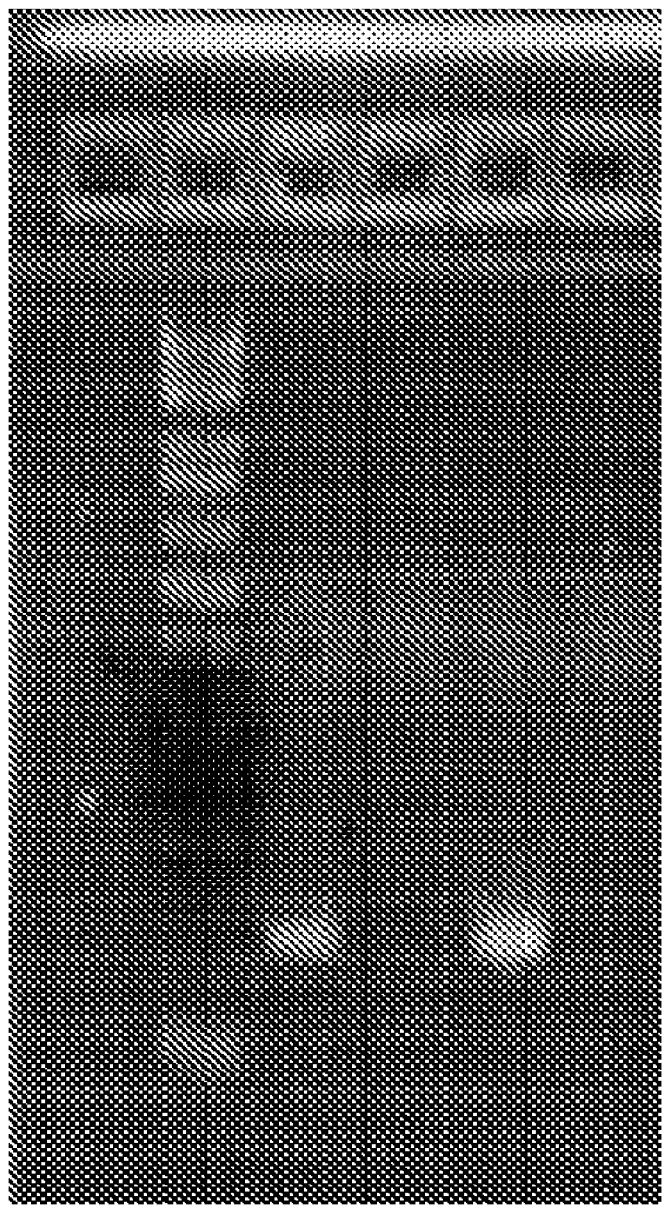

FIG. 8C demonstrates that PrimeStore™ is impervious to nuclease digestion. Gel electrophoresis of post-amplified product. Lane 3 is the PCR product from template RNA+ PrimeStore™ at 37° C. for 7 days, and Lane 5 amplification of positive control RNA. Lane 5 (no amplification) is RNA without PrimeStore™ Lane 2 and 6 are 100 bp ladder, and NTC reactions, respectively.

Figure 9:
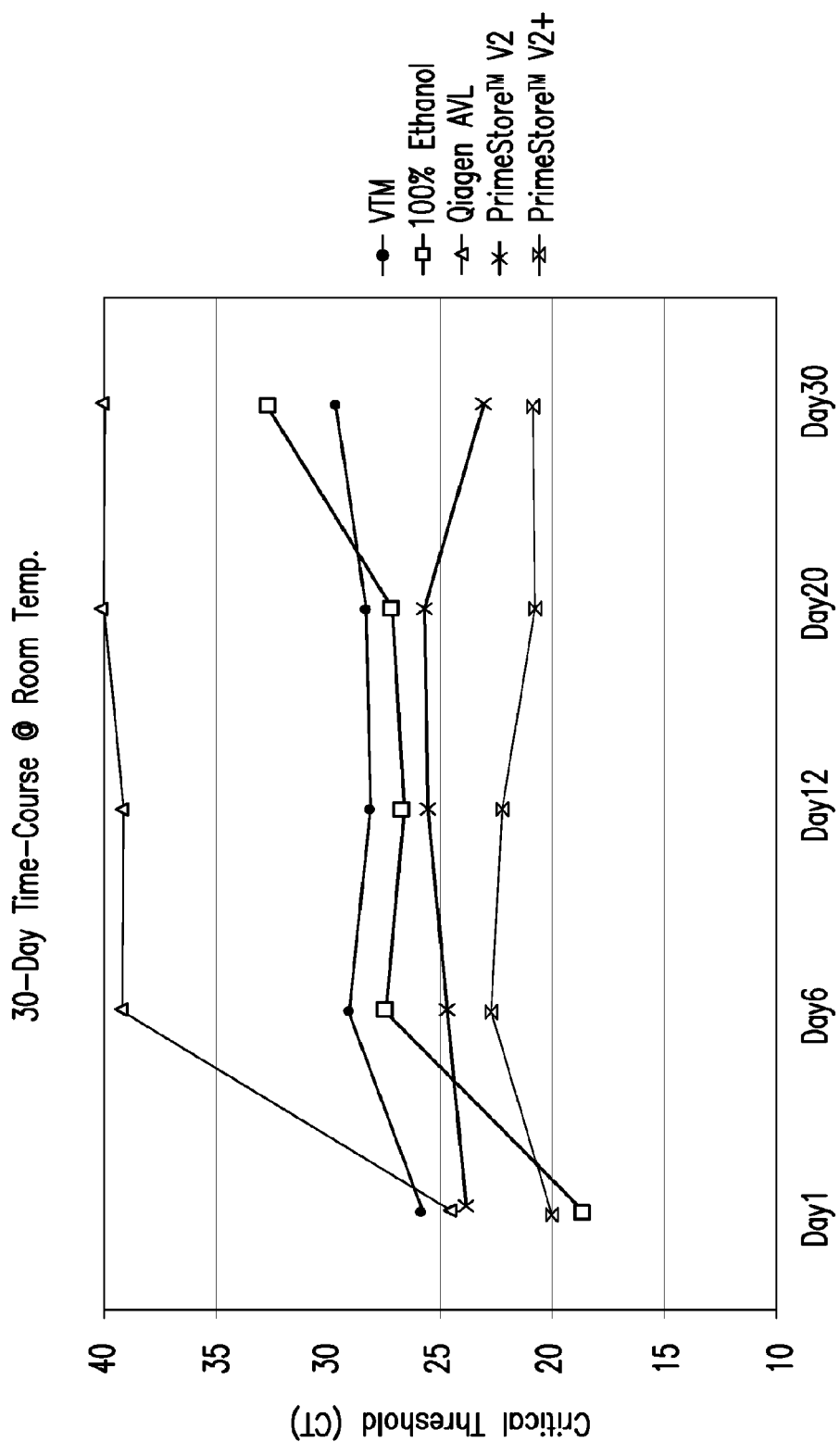

FIG. 9 illustrates that PrimeStore™ preservation is superior to other solutions. PrimeStore™ (Ver. 2 and Ver. 2.2) Preservation of RNA from influenza A virus compared to Qiagen AVL buffer, ethanol, and Viral Transport Media (VTM) at ambient temperature (22-25° C.) for 30 days.

Figure 10:
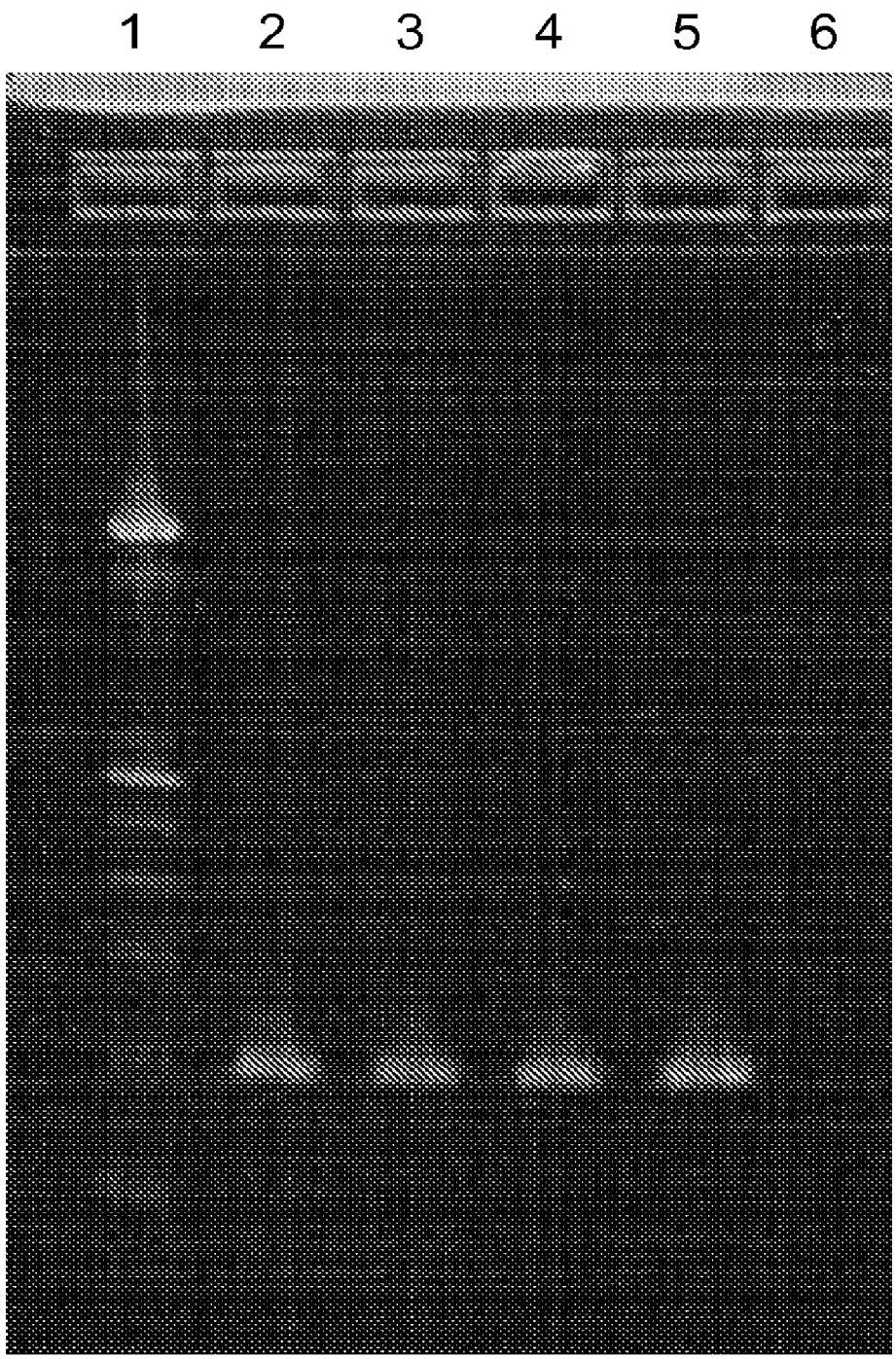

FIG. 10 shows the extraction efficiency of Influenza A virus preserved in PrimeStore™ (Ver. 2.2) for 30 days at various temperatures. Environmental (21-37° C.); Freeze-thawed (−25° C.; 32×); ambient temperature (22-26° C.); and Lane 5: refrigerated (4° C.).

Figure 11:
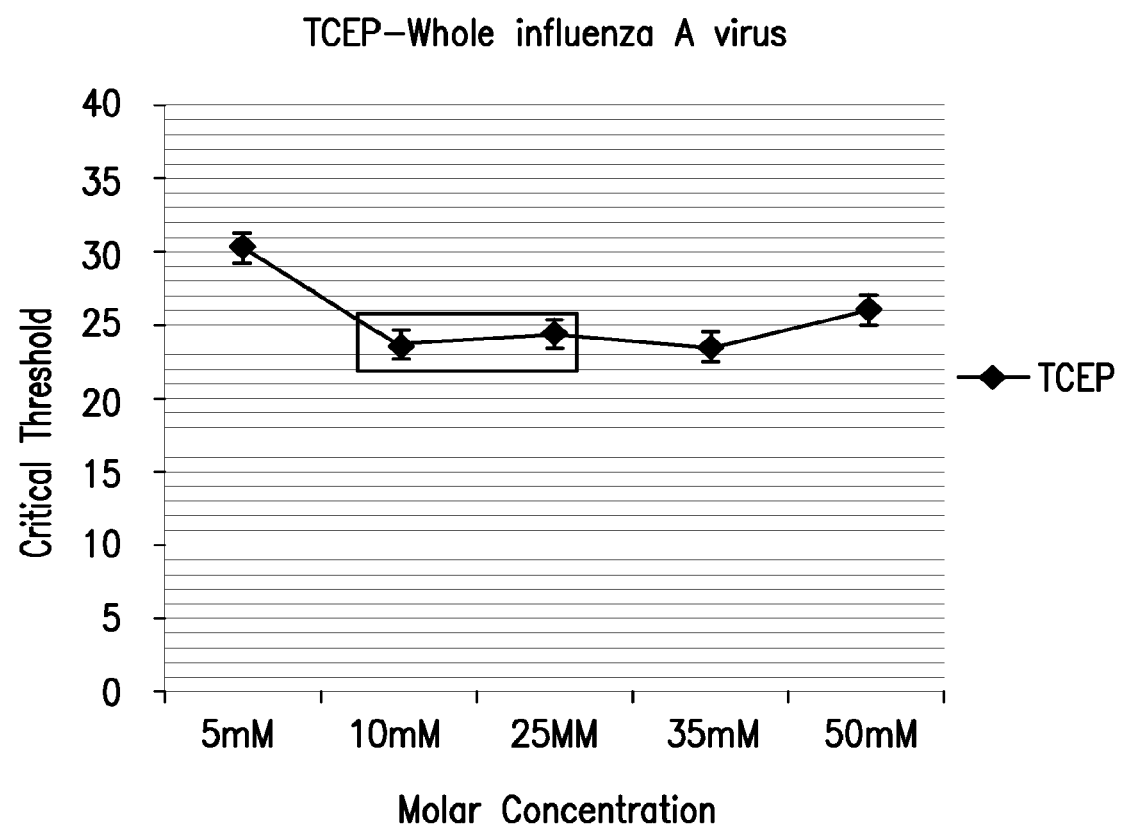
Figure 13A:
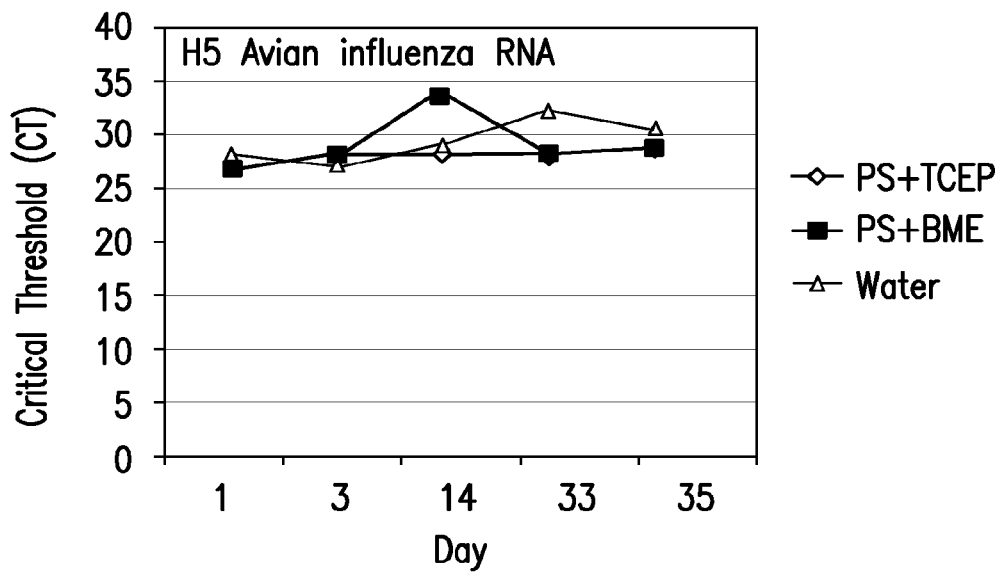
Figure 13B:
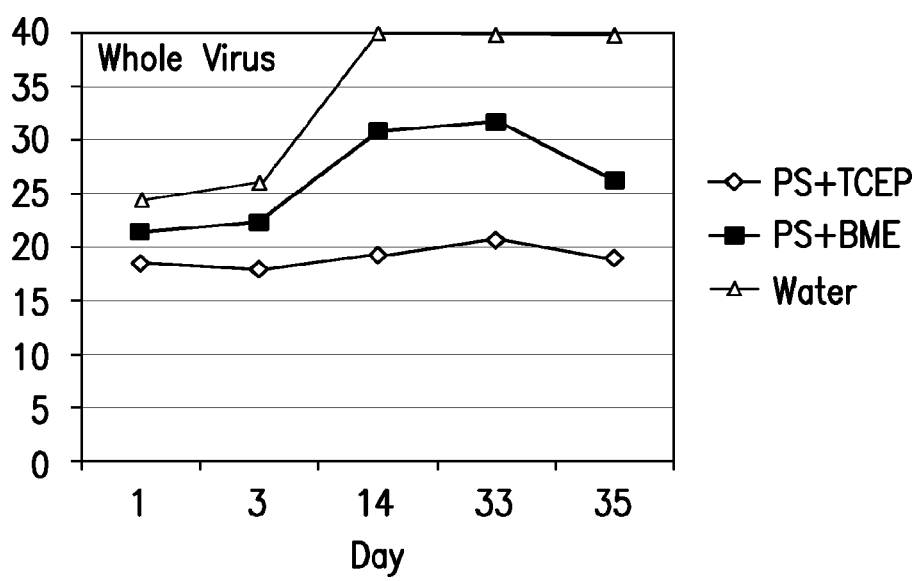

FIG. 11 is a graph of critical threshold vs. molar concentration using whole influenza A virus with TCEP as the reducing agent;

Figure 12:
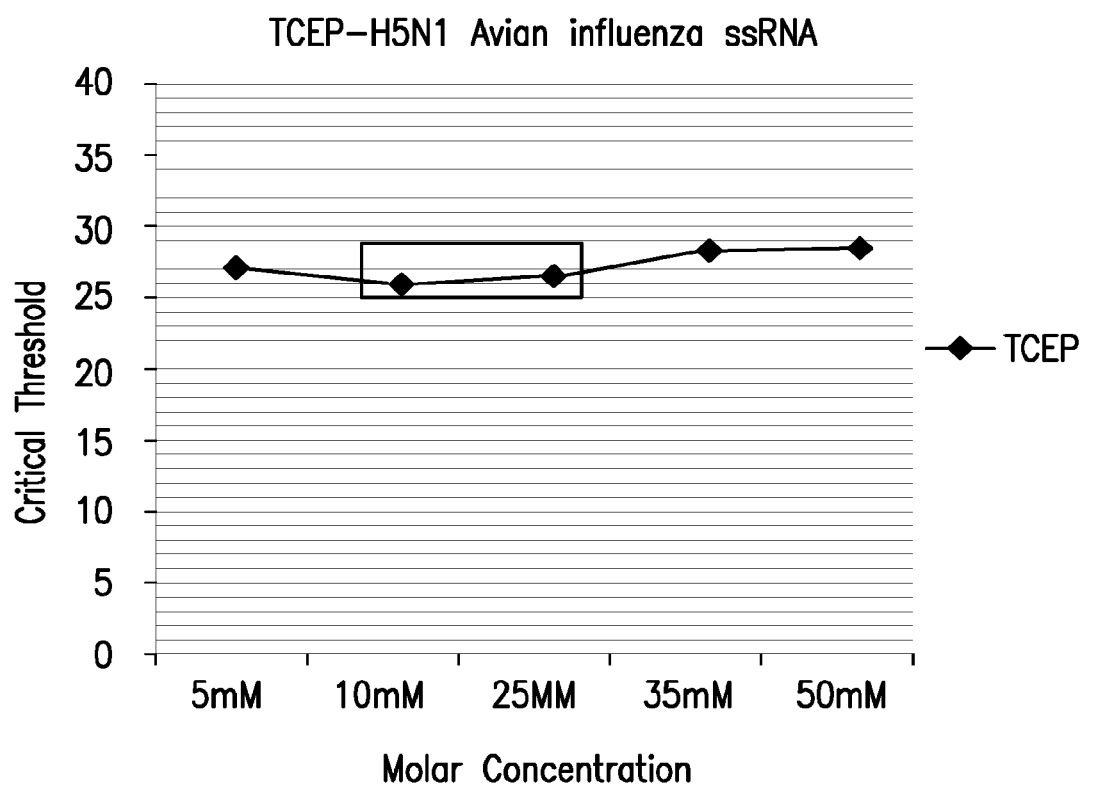

FIG. 12 is a graph of the critical threshold vs. molar concentration using H5N1 Avian influenza ssRNA with TCEP as the reducing agent;

FIG. 13A and FIG. 13B show the comparison between TCEP and β-ME as reducing agent components of the PrimeStore™ Solution compositions, using a water only control. In FIG. 13A, H5 avian influenza RNA was employed, while in FIG. 13B, whole virus were used.

Figure 14A:
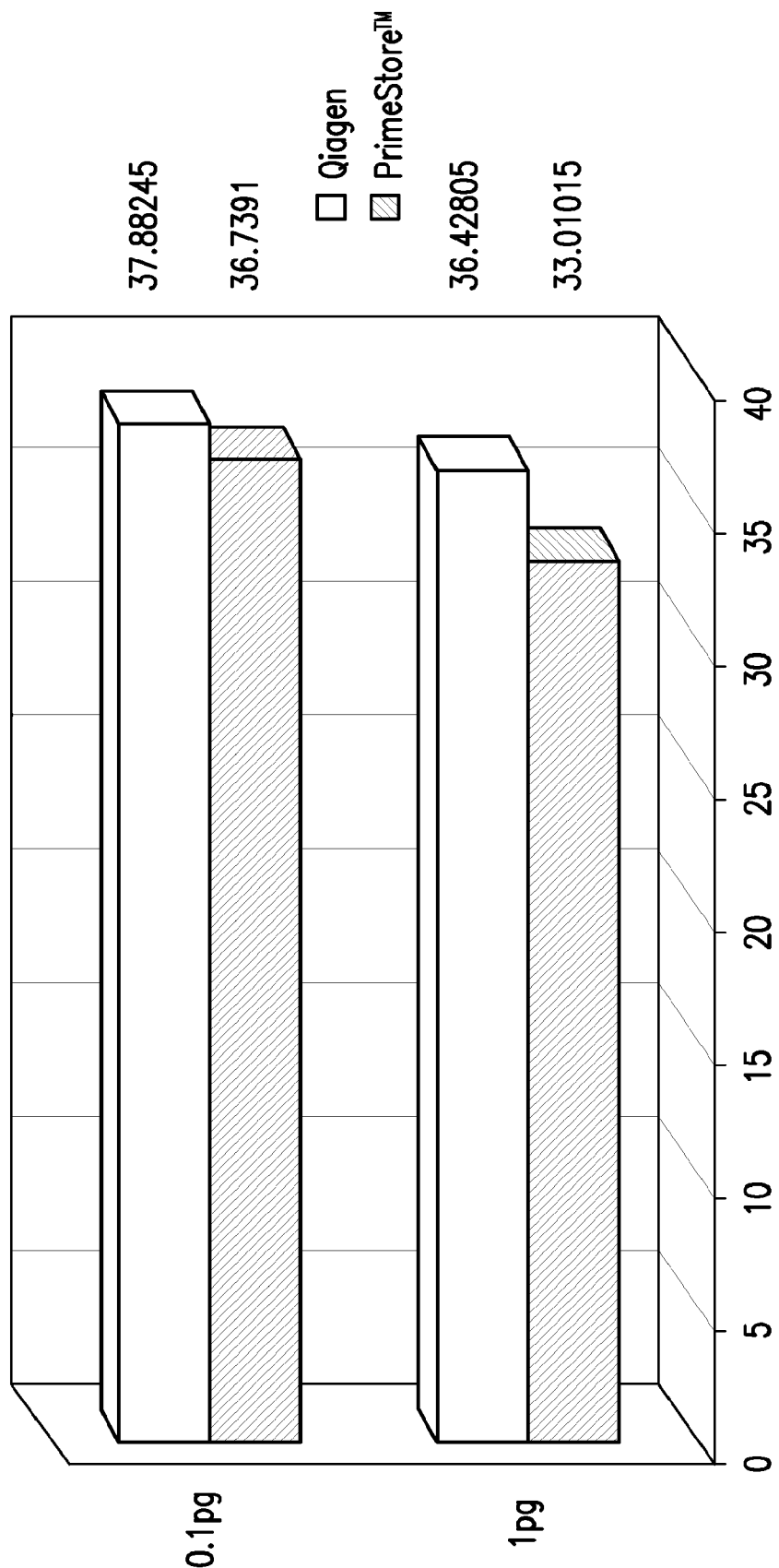

FIG. 14A shows the results of a study employing PrimeStore™ solution in preserving nucleic acids from blood. PrimeStore Extraction Efficiency of whole blood spiked with RNA compared to the lysis solution in the QIAamp® DNA Blood Mini Kit. 0.1 pg and 1 pg of influenza A RNA were spiked and extracted using PrimeStore™ or AL Lysis buffer. At both RNA concentrations, PrimeStore™ produced superior results as evident by real-time RT-PCR CT scores;

FIG. 14B tabulates data from the study shown in FIG. 14A involving the extraction of "naked" H5 avian influenza ssRNA from blood tubes. PrimeStore™ Extraction Efficiency of whole blood spiked with RNA compared to the lysis solution in the QIAamp® DNA Blood Mini Kit using different blood anticoagulants. PrimeStore™ was superior compared to the AL Lysis Buffer from Qiagen using Blood spiked with RNA in common anticoagulant blood-collection tubes; and FIG. 14C tabulates data from the study shown in FIG. 14A involving the comparison of in PrimeStore™ Solution vs. a commercial extraction kit (Qiagen). Shown is the Extraction Efficiency of PrimeStore™ for whole blood spiked with RNA compared to the lysis solution in the QIAamp® DNA Blood Mini Kit. 0.1 pg and 1 pg of Influenza A viral RNA were spiked and extracted using PrimeStore or AVL Lysis buffer. At both RNA concentrations, PrimeStore™ produced superior results as evident by real-time RT-PCR CT scores.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The extended stabilization, collection, transport, and preservation imparted by the disclosed formulations are particularly advantageous when a sample or specimen is located in a geographical region that is remote from a testing facility. Remote locations, also referred to as field sites, encompass a variety of environments where diagnostic testing is typically not performed. These sites include doctors' offices, triage centers, airports, border crossings, outbreak areas, and a variety of outdoor locations. The disclosed compositions and methods for their use offer particular advantages in locations where there is no access to electricity and/or refrigeration, or where access is inconsistent. Because of the extended stability at room temperature, a sample can be taken from any remote location, for example without limitation at a malarial outbreak site in Africa, and the sample can be shipped to the United States or Europe for diagnostic analysis in a laboratory. Because the disclosed collection formulations are stable at room temperature or below, and preferably even at tropical or subtropical temperatures for a time, they can routinely be taken into the field without worry that the component reagents (such as RNA controls) themselves will degrade until a sample can be analyzed, typically at a remote location from the collection.

The compositions of the invention may be any suitable aqueous formulation as described herein, including but not limited to a solution, suspension (incl. colloidal suspension), slurry, emulsion, homogenate, or the like. A preferred aqueous formulation is a solution, and therefore the term "solution" has been used in the exemplary sense throughout the detailed description of the preferred embodiments to refer to any of the aqueous compositions of the invention.

Specimen Collection for Clinical Diagnostic Laboratories

Collection is first step in diagnostic platforms or molecular protocols requiring the detection of potentially minute amounts of nucleic acids from pathogens including viruses. To facilitate the dynamic advancements in nucleic acid based detection strategies and their integration into the mainstream diagnostic laboratories there is a colossal need for reliable, robust, and standardized collection systems developed specifically with the intent of being utilized for downstream nucleic acid based detection such as the aforementioned platforms. The invention can alternatively be adapted for transport of nucleic acids from a doctor's office or operating room, or alternatively transported to a regional center, such as a hospital.

A clinical or veterinary specimen or a forensic or environmental sample collection system may include one or more collection tools and one or more reagents for efficiently: 1) obtaining a high yield of suitable specimen beyond what is currently available in the art; 2) inactivating potentially infectious biological pathogens so that they are no longer viable and can be handled; shipped, or transported with minimal fear of pathogen release or contamination; or 3) effectively stabilizing and preserving lysed 'naked' RNA/DNA polymers from hydrolysis or nuclease degradation for prolonged periods at ambient temperatures until samples can be processed at a diagnostic laboratory, and preferably for achieving two or more, or all three, of these goals.

The collection/transport solutions of the present invention can provide a number of improvements and benefits over those presently available in the art. Exemplary benefits include, without limitation, one or more of the following:

Inactivation, killing, and/or lysis of microbes, viruses, or pathogens;

Destruction and/or inactivation of exogenous or endogenous nucleases, including, without limitation, RNase and/or DNase;

Compatibility with a variety of conventional nucleic acid extraction, purification, and amplification systems;

Preservation of RNA and/or DNA integrity within the sample;

Facilitation of transport and shipping at ambient temperatures, even over extended periods of time, or extreme temperature variations; and Suitability for short—(several hours to several days), intermediate—(several days to several weeks), or long—(several weeks to several months) term storage of the isolated nucleic acids.

The disclosed compositions are particularly well suited for point-of-care, field studies, in-home health care or testing, triage/emergency and casualty assessment(s), mobile forensics, pathology, epidemiological sampling, crime scene investigation, paternity testing, pre- and post-pregnancy genetic screening, rape/incest testing and family counseling, confidential screening and testing for sexually transmitted diseases, including, without limitation, HIV, syphilis, *Chlamydia*, gonorrhoeae, or other venereal diseases and the like, and may be of particular value during the monitoring, etiology, and control of epidemic or pandemic diseases in both human and animal populations domestically and abroad. The compositions may be of particular relevance in collecting and analyzing Influenzavirus samples, including without limitation to predict and help manage shift and drift and to manage an imminent or ongoing pandemic.

In certain embodiments, the nucleic acid(s) isolated by the methods of the present invention may serve as a template in one or more subsequent molecular biological applications, assays, or techniques, including, without limitation, genetic fingerprinting; amplified fragment length polymorphism (AFLP) polymerase chain reaction (PCR); restriction fragment length polymorphism analysis (RFLP); allele-specific oligonucleotide analysis (ASOA); microsatellite analysis; Southern hybridization; Northern hybridization; variable number of tandem repeats (VNTR) PCR; dot-blot hybridization; quantitative real-time PCR; polymerase cycling assembly (PCA); nested PCR; quantitative PCR (Q-PCR); asymmetric PCR; DNA footprinting; single nucleotide polymorphism (SNP) genotyping; reverse transcription PCR (RT-PCR); multiplex PCR (m-PCR); multiplex ligation-dependent probe amplification (MLPA); ligation-mediated PCR (LmPCR); methylation specific PCR (MPCR); helicase-dependent amplification (HDA); overlap-extension PCR (OE-PCR); whole-genome amplification (WGA); plasmid isolation; allelic amplification; site-directed mutagenesis; high-throughput genetic screening; or the like, or any combination thereof.

The compositions of the present invention provide clinical/environmental collection solutions that efficiently achieve at least three, and preferably all four of the following: 1) kill or inactivate potentially-infectious pathogens, so that they are non-viable and can be safely handled, shipped or transported; 2) lyse cells to release RNAs and/or DNAs from the biological specimen contained in the collection system; 3) protect the released or 'naked' polynucleotides in the sample from further hydrolysis or enzymatic degradation, modification, or inactivation; and 4) prolong the conventional time-frame for storage and transportation of the processed sample under a variety of ambient, sub- or supra-optimal temperature conditions to maintain the fidelity and integrity of the released polynucleotides until the biological material can be further processed or analyzed at a diagnostic facility or analytical laboratory.

In one exemplary embodiment, the methods and formulations maintain at least substantial stability of the nucleic acids in the sample for an extended period of time, e.g., for up to about 15 days, preferably up to about 30 days, or more preferably up to about 60 days or more, without refrigeration or freezing of the sample, and even when stored at room temperature, or ambient environmental conditions including those of temperate, sub-tropical or tropical climates and the like. In other embodiments, use of the disclosed compositions to prepare nucleic acids from a sample of biological origin is desirable to maintain at least substantial integrity and fidelity of the nucleic acids released from the sample for extended periods including, without limitation, at least about 5 to about 15 days, preferably at least about 10 to 20 days, more preferably at least about 15 to 25 days, or more preferably still, at least about 20 to 30 days or more, without a requirement for refrigerating or freezing the sample either at the time of sample collection or until the sample is further processed (or both) hours, days, weeks, or even months after originally being collected and placed into the disclosed storage/collection/transport/stabilization formulations.

Nucleic acids obtained from biological samples in the practice of the disclosed methods are advantageously compatible with a number of conventional molecular and diagnostic isolation, purification, detection, and/or analytic methodologies. The disclosed compositions facilitate recovery storage, and transport of populations of stabilized, substantially non-degraded, polynucleotides for use in a variety of subsequent methodologies, including, without limitation, nucleic acid isolation, purification, amplification, and molecular analytical and/or diagnostic testing, assay, analysis, or characterization, and the like.

Exemplary Commercial Kits of the Present Invention

Figure 5:
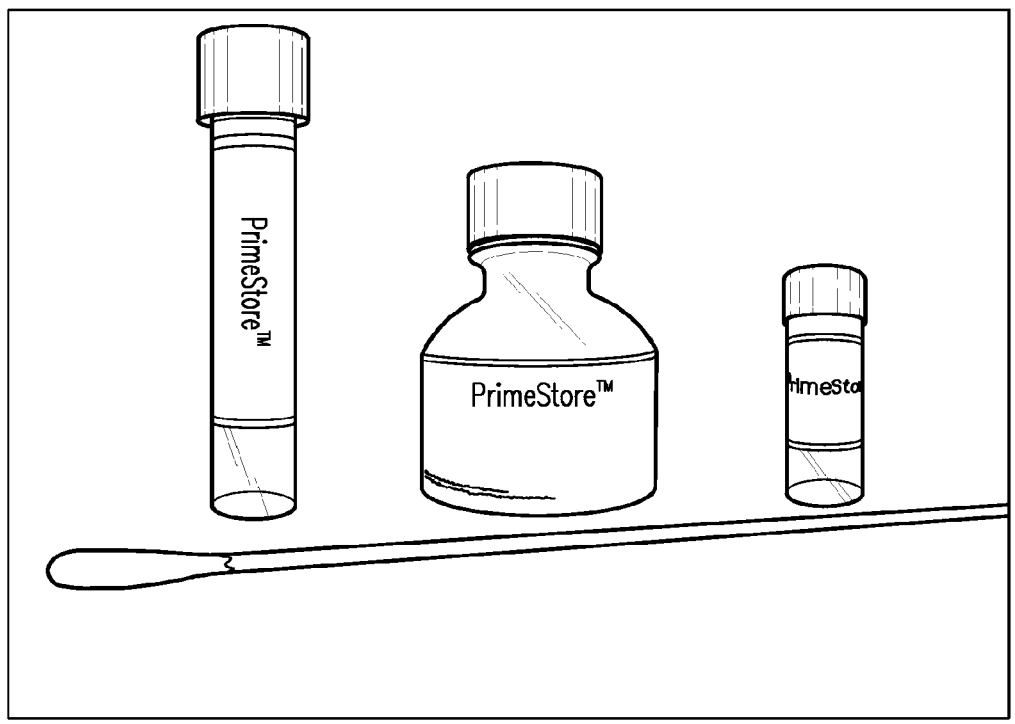
FIG. 5 shows an exemplary commercial PrimeStore™ Collection Solution. Three exemplary commercial collection solution formats: 25 mL bottle, and the 5 mL and 1.5 mL tube formats.

The following outline provides exemplary commercial kits employing the PrimeStore™ compositions of the present invention (FIG. 5).

Peel-Pouch Collection System

Five-mL tube containing 1.5 mL PrimeStore™ Solution; Collection swab (e.g., FlockedSWABS® [Copan Diagnostics, Inc., Murrieta, Calif., USA]); and instructions for collection and/or processing of samples. (packed, e.g., in 50 pouches/unit) (See FIG. 4A, FIG. 4B, FIG. 4C, FIG. 4D, and FIG. 4E for a schematic demonstration of such systems).

PrimeStore™ Stock Solution (e.g., 25-mL bottles)

Once formulated, PrimeStore™ stock solution is stable at 4° C. or below for periods of at least one year or more. Formulated PrimeStore™ Solution has also been shown to be stable at ambient temperature (e.g., about 20-30° C.) for periods of three to six months or more.

Once a sample is contacted with a PrimeStore™ formulation as disclosed herein, it can reasonably expected to be stored indefinitely at temperatures of 0° C. or below, at least one year or more under refrigeration (e.g., 4° C. and at least 30 days or more at ambient temperature (e.g., about 20-30° C.), without significant loss of nucleic acid composition, fidelity or integrity of the sample. For example, without limitation, the integrity of a population of polynucleotides obtained from the sample is at least substantially maintained, and preferably entirely maintained without detectable degradation, when the composition comprising the sample is stored at a temperature of from about −20° C. to about 40° C., for a period of from about 30 days to about 60 days.

The kit may also include one or more vials including the inventive compositions and one or more extraction devices to help liberate and separate the nucleic acids to obtain at least substantially pure RNA/DNA to be analyzed.

Environmental Sample and Storage Systems 0.1-, 0.2-, 0.5-, 1-, 2-, or 3-mL collection vials each containing 0.1 mL, 0.2 mL, 0.25 mL, 0.5 mL, 0.75 mL, or 1 mL PrimeStore™ solution; and instructions for collection and/or processing of samples (packed, e.g., 10 vials/unit). The collection vials may be sized larger as needed depending on the proposed collection method.

Definitions

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal or acceptable for a diagnostic purpose, as applicable. The use of one or more delivery vehicles for chemical compounds in general, and peptides and epitopes in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed immunogenic compositions.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (snRNA), small nucleolar RNA (snORNA), small nuclear RNA (snRNA), and small temporal RNA (stRNA), and the like, and any combination thereof.

As used herein, the terms "protein," "polypeptide," and "peptide" are used interchangeably, and include molecules that include at least one amide bond linking two or more amino acid residues together. Although used interchangeably, in general, a peptide is a relatively short (e.g., from 2 to about 100 amino acid residues in length) molecule, while a protein or a polypeptide is a relatively longer polymer (e.g., 100 or more residues in length). However, unless specifically defined by a chain length, the terms peptide, polypeptide, and protein are used interchangeably.

As used herein, "sample" includes anything containing or presumed to contain a substance of interest. It thus may be a composition of matter containing nucleic acid, protein, or another biomolecule of interest. The term "sample" can thus encompass a solution, cell, tissue, or population of one of more of the same that includes a population of nucleic acids (genomic DNA, cDNA, RNA, protein, other cellular molecules, etc.). The terms "nucleic acid source," "sample," and "specimen" are used interchangeably herein in a broad sense, and are intended to encompass a variety of biological sources that contain nucleic acids, protein, one or more other biomolecules of interest, or any combination thereof. Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluid from cysts or abcess contents, synovial fluid, vitreous or aqueous humor, eye washes or aspirates, pulmonary lavage or lung aspirates, and organs and tissues, including but not limited to, liver, spleen, kidney, lung, intestine, brain, heart, muscle, pancreas, and the like, and any combination thereof. In some embodiments, the sample may be, or be from, an organism that acts as a vector, such as a mosquito, or tick, or other insect(s).

Tissue culture cells, including explanted material, primary cells, secondary cell lines, and the like, as well as lysates, homogenates, extracts, or materials obtained from any cells, are also within the meaning of the term "biological sample," as used herein. Microorganisms (including, without limitation, prokaryotes such as the archaebacteria and eubacteria; cyanobacteria; fungi, yeasts, molds, actinomycetes; spirochetes, and mycoplasmas); viruses (including, without limitation the Orthohepadnaviruses [including, e.g., hepatitis A, B, and C viruses], human papillomavirus, Flaviviruses [including, e.g., Dengue virus], Lyssaviruses [including, e.g., rabies virus], Morbilliviruses [including, e.g., measles virus], Simplexviruses [including, e.g., herpes simplex virus], Polyomaviruses, Rubulaviruses [including, e.g., mumps virus], Rubiviruses [including, e.g., rubella virus], Varicellovirus [including, e.g., chickenpox virus], rotavirus, coronavirus, cytomegalovirus, adenovirus, adeno-associated virus, baculovirus, parvovirus, retrovirus, vaccinia, poxvirus, and the like), algae, protozoans, protists, plants, bryophytes, and the like, and any combination of any of the foregoing, that may be present on or in a biological sample are also within the scope of the invention, as are any materials obtained from clinical or forensic settings that contain one or more nucleic acids are also within the scope of the invention. The ordinary-skilled artisan will also appreciate that lysates, extracts, or materials obtained from any of the above exemplary biological samples are also within the scope of the invention.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "biological molecule" refers to any molecule found within a cell or produced by a living organism, including viruses. This may include, but is not limited to, nucleic acids, proteins, carbohydrates, and lipids. As used herein, a "cell" refers to the smallest structural unit of an organism that is capable of independent functioning and is comprised of cytoplasm and various organelles surrounded by a cell membrane. This may include, but is not limited to, cells that function independently such as bacteria and protists, or cells that live within a larger organism such as leukocytes and erythrocytes. As defined herein, a cell may not have a nucleus, such as a mature human red blood cell.

Samples in the practice of the invention can be used fresh, or can be used after being stored for a period of time, or for an extended period of time, including for example, cryopreserved samples and the like, and may include material of clinical, veterinary, environmental or forensic origin, may be isolated from food, beverages, feedstocks, potable water sources, wastewater streams, industrial waste or effluents, natural water sources, soil, airborne sources, pandemic or epidemic populations, epidemiological samples, research materials, pathology specimens, suspected bioterrorism agents, crime scene evidence, and the like.

As used herein, the term "patient" (also interchangeably referred to as "host" or "subject") refers to any host that can serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner. The invention may also be used to monitor disease outbreak, progression, and epidemiological statistics for a variety of global populations, including, without limitation, wasting disease in ungulates, tuberculosis, ebola, SARS, and avian influenzas. In certain embodiments, the samples will preferably be of mammalian origin, and more preferably of human origin.

The term "chaotrope" or "chaotropic agent" as used herein, includes substances that cause disorder in a protein or nucleic acid by, for example, but not limited to, altering the secondary, tertiary, or quaternary structure of a protein or a nucleic acid while leaving the primary structure intact.

The term "e.g.," as used herein, is used merely by way of example, without limitation intended, and should not be construed as referring only those items explicitly enumerated in the specification.

The term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

In accordance with long standing patent law convention, the words "a" and "an" when used in this application, including the claims, denotes "one or more."

EXAMPLES

The following examples are included to demonstrate illustrative embodiments of the invention. It should be appreciated by those of ordinary skill in the art that the techniques disclosed in the examples that follow represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Formulation of Exemplary Storage Solutions

The present example provides a general formulation of the PrimeStore™ (PanFlu) compositions of the present invention. Exemplary formulations are also detailed in Examples 2-5.

Materials

Guanidine thiocyanate, sodium citrate, Antifoam A® Concentrate, and N-lauroylsarcosine, sodium salt, were all purchased from Sigma Chemical Co. (St. Louis, Mo., USA). Tris(2-carboxyethyl) phosphine hydrochloride (TCEP) was obtained from Soltec Ventures Inc. (Beverly, Mass., USA). 2-amino-2-hydroxymethyl-propane-1,3-diol (TRIS) was obtained from Applied Biosystems/Ambion (Austin, Tex., USA). 2-[2-(Bis(carboxymethyl)amino)ethyl-(carboxymethyl)amino]acetic acid (EDTA) GIBCO® Ultra Pure was obtained from Invitrogen Corp. (Carlsbad, Calif., USA). All other reagents are available commercially from Sigma-Aldrich or USB Corporation.

TABLE 1

FORMULATION RANGES OF EXEMPLARY COMPONENTS FOR THE PREPARATION OF PRIMESTORE ™ COMPOSITIONS

| Reagent | Component Final Concentration Ranges |
|---|---|
| 1. A chaotrope, e.g.: | |
| Guanidine thiocyanate | about 0.5M to about 6M |
| or Guanidine hydrochloride | about 0.5M to about 6M |
| or Guanidine isocyanate | about 0.5M to about 6M |
| 2. An anionic detergent, e.g.: | |
| N-lauroyl sarcosine (inter alia Na salt) | about 0.15% to about 1% (wt./vol.) |
| or Sodium dodecyl sulfate, | Same |
| Lithium dodecyl sulfate, | Same |
| Sodium glycocholate, | Same |
| Sodium deoxycholate, | Same |
| Sodium taurodeoxycholate, or | Same |
| Sodium cholate | about 0.1% to about 1% (wt./vol.) |
| 3. A reducing agent, e.g.: | |
| TCEP | about 0.5 mM to about 30 mM |
| or β-ME, DTT, formamide, or DMSO | about 0.05M to about 0.3M |

TABLE 1-continued

FORMULATION RANGES OF EXEMPLARY COMPONENTS FOR THE PREPARATION OF PRIMESTORE ™ COMPOSITIONS

| Reagent | Component Final Concentration Ranges |
|---|---|
| 4. A chelator, e.g.: | |
| Sodium citrate | about 0.5 mM to about 50 mM |
| or EDTA, EGTA, HEDTA, DTPA, NTA, or APCA | about 0.01 mM to about 1 mM |
| 5. A buffer (e.g., TRIS, HEPES, MOPS, MES, Bis-Tris, etc.) | about 1 mM to about 1M |
| 6. An acid (e.g., HCl or citric acid) | q.s. to adjust to a pH of about 6 to 7, preferably 6.4 to 6.8 |
| 7. Nuclease-free water | q.s. to desired final volume |
| Optionally one or more of: | |
| 8. A surfactant/defoaming agent, e.g.: Antifoam A ® or Tween ® | about 0.0001% to about 0.3% (wt./vol.) |
| 9. An alkanol (e.g, methanol, ethanol, propanol, etc.) | about 1% to about 25% (vol./vol.) |
| 10. RNA or DNA | about 1 pg to about 1 µg/mL |

Example 2

Formulation of an Exemplary Storage Solution

The present example describes a first exemplary formulation of the compositions of the invention. This formulation has also been alternatively referred to by the inventors as "PrimeStore™ Solution" or "PSS" version 1.

TABLE 2

PREPARATION OF PRIMESTORE ™ COMPOSITION (VER. 1)

| Reagent | Final Concentration |
|---|---|
| Guanidine thiocyanate | 4M |
| Sodium citrate | 30 mM |
| Sodium dodecyl sulfate | 0.25% (wt./vol.) |
| N-lauroyl sarcosine, sodium salt | 0.25% (wt./vol.) |
| 2-mercaptoethanol (β-ME) | 0.1M |
| Antifoam A | 0.1% (wt./vol.) |

TABLE 2-continued

PREPARATION OF PRIMESTORE ™ COMPOSITION (VER. 1)

| Reagent | Final Concentration |
|---|---|
| Citric acid | q.s. to adjust pH to 6.5 |
| Nuclease-free water | 11.82 mL |

Example 3

Preparation of a Second Exemplary Storage Solution

The present example describes the preparation of another exemplary storage solution according to the present invention. This formulation has also been alternatively referred to by the inventors as PrimeStore™ version 2.

TABLE 3

PREPARATION OF PRIMESTORE ™ COMPOSITION (VER. 2)

| Reagent | Quantity | Final Concentration |
|---|---|---|
| Guanidine thiocyanate | 35.488 gm | 3M |
| TCEP | 0.02867 gm | 1 mM |
| Sodium citrate | 0.2931 gm | 10 mM |
| N-lauroyl sarcosine, sodium salt (NLS) | 0.5 gm | 0.5% |
| Antifoam A (10% solution) | 200 µL | 0.002% |
| TRIS (1M) | 10 mL | 100 mM |
| EDTA (0.5M) | 20 µL | 0.1 mM |
| Hydrochloric acid (HCl) | q.s. to adjust pH to 6.7 | — |
| Nuclease-free water | q.s. to 100 mL | — |

Example 4

Preparation of a Third Exemplary Storage Solution

The present example describes the preparation of another exemplary storage solution according to the present invention. This formulation has also been alternatively referred to by the inventors as PrimeStore™ version 2.2.

TABLE 4

PREPARATION OF PRIMESTORE ™ COMPOSITION (VER. 2.2)

| Reagent | Quantity | Final Concentration |
|---|---|---|
| Guanidine thiocyanate | 35.488 gm | 3M |
| TCEP | 0.02867 gm | 1 mM |
| Sodium citrate | 0.2931 gm | 10 mM |
| N-lauroyl sarcosine, sodium salt (NLS) | 0.5 gm | 0.5% |
| Antifoam A (10% solution) | 200 µL | 0.002% |
| TRIS (1M) | 10 mL | 100 mM |
| EDTA (0.5M) | 20 µL | 0.1 mM |
| Ethanol, molecular grade (96-100%) | 23 mL | 23% (vol./vol.) |
| Hydrochloric acid (HCl) | q.s. to adjust pH to 6.7 | — |
| Nuclease-free water | q.s. to 100 mL | — |

Exemplary Protocol for Preparation of PrimeStore Solution (ver. 2.2)

1. Add 40 mL of nuclease-free water to a clean beaker with a stir bar.
2. Place beaker on a hot plate/stirrer and adjust temperature to 60-65° C. Set stirring speed to medium.
3. Add 35.488 gm of guanidine thiocyanate slowly to the water allowing it to dissolve as added.
4. Add 0.0287 gm of TCEP to beaker and increase stirrer speed to help dissolve crystals.
5. Add 0.2931 gm of sodium citrate to the beaker.
6. Add 0.5 gm of NLS to the solution. Increase stirrer speed to create a vortex in the beaker. This will pull the NLS into the solution and help dissolve the reagent.

TABLE 4-continued

PREPARATION OF PRIMESTORE™ COMPOSITION (VER. 2.2)

7. Vortex a prepared 10% Antifoam A solution (1 mL Antifoam A Concentrate + 9 mL nuclease-free water). Pipette 200 µL of the 10% Antifoam A into the solution.
8. Pipette 10 mL of 1M TRIS into the solution.
9. Pipette 20 µL of 0.5M EDTA into the solution.
10. Increase the temperature to bring the solution to 75-80° C. and stir for 3-5 minutes.
11. Remove beaker from heat and allow solution to cool to room temperature (≈22-25° C.).
12. Add 23 mL of ethanol to the solution and mix thoroughly.
13. Adjust pH to 6.7 with HCl.
14. Pour solution into a clean 100 mL graduated cylinder.
15. Add nuclease-free water to bring total volume to 100 mL.
16. Transfer solution to a labeled sterile container. Store at room temperature (≈22-25° C.).

*Note:
Preferably, make sure each reagent is completely dissolved before adding the next.

Example 5

Comparison of PrimeStore™ Solutions to Conventional Formulations

Figure 1:
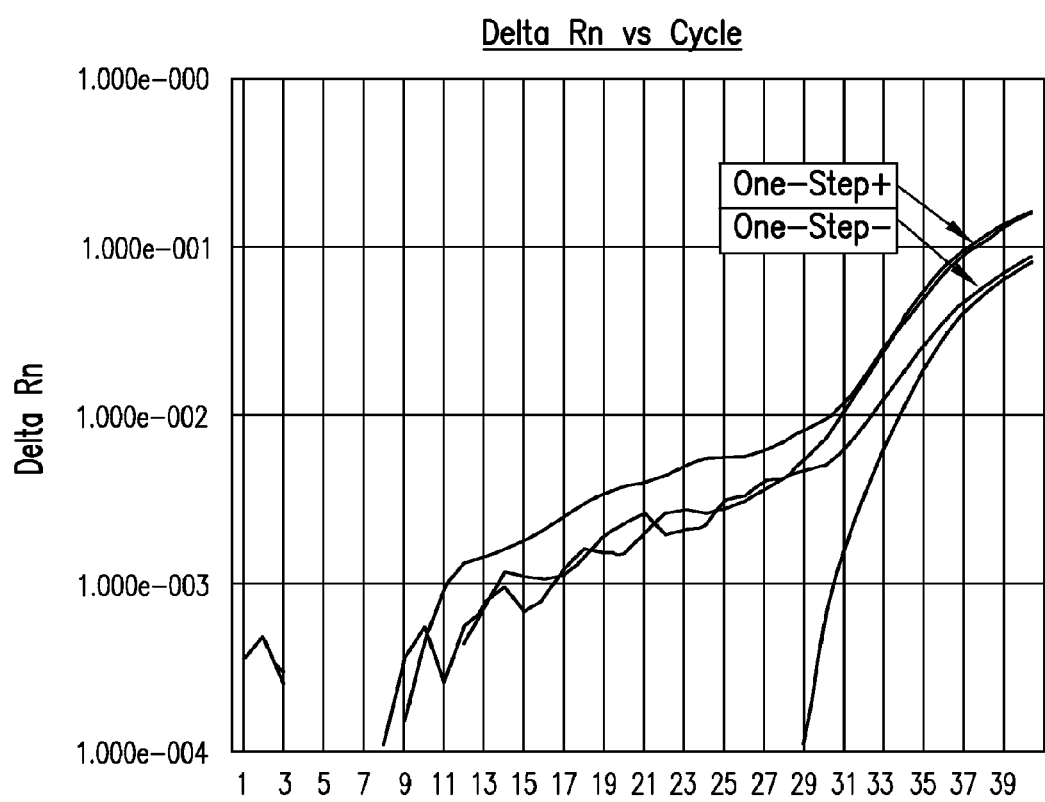
FIG. 1 shows the extraction efficiency of PrimeStore™ (ver. 1). PrimeStore (ver. 1 [depicted here as "One-step+"]) compared to the Lysis Solution provided in the RNaqueous®-Micro Kit (Ambion, Cat#AM1931) using a standard amount of whole influenza A virus. For the comparison either the one-step formulation or the Lysis Solution provided in the kit was used for viral RNA lyses and then extracted according to manufacturer protocols. Replicate reactions were processed and analyzed by real-time RT-PCR (rRT-PCR) using an ABI 7500 sequence detection system.
Figure 4A:
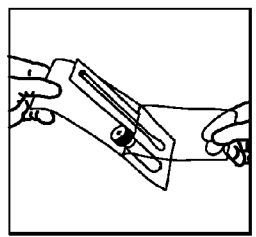
(FIG. 4A). Directions of sample collection using a clinical collection swab (Copan Diagnostics) (FIG. 4B) and a 5 mL collection tube (FIG. 4C) containing 1.5 mL of PrimeStore™ Solution, and a schematic demonstration of the manipulation of the system (FIG. 4D and FIG. 4E).
Figure 4B:
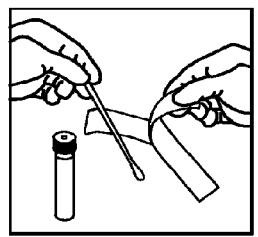
FIG. 4 shows an example of a PrimeStore™ packaging format for clinical diagnostic collection.
Figure 4C:
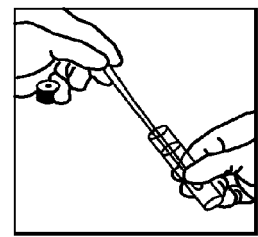
Figure 4D:
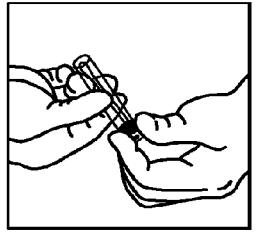
Figure 4E:
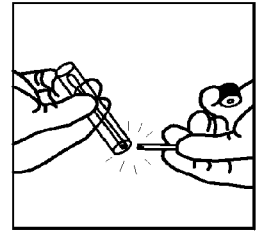

A sample of homogenized nasal tissue from a cotton rat (*Sigmodon hispidus*) challenged with influenza A (H3N2) or a human clinical influenza A (H1N1) sample collected as a human clinical nasal wash during the 2006-07 season were placed in PrimeStore™ Solution (Ver. 1) and tested compared to the respective lysis formulation and protocol, and extraction procedure, from three commercially available kits: RNAqueous®-Micro (Ambion, Austin, Tex., USA), QIAamp Viral RNA Mini Kit (Catalogue #52904, Qiagen, Valencia, Calif., USA), and MagMax AI/ND Viral RNA Isolation Kit (Catalogue #AM1929, Ambion). Extraction efficiency was evaluated using the ABI 7500 sequence detection system with the comparative threshold cycle ($C_T$) method (See FIG. 2). In FIG. 2, "delta Rn" represents the fluorescent reporter signal minus a baseline amount. As shown in FIG. 1 and FIG. 2, the relative $C_T$ scores and viral copies detected were optimal when the fixing formulation was used in place of the respective conventional lysis buffer for each commercial kit. In these two sample types, the compositions of the invention worked better than the two conventional Kits for extraction purposes. The PrimeStore™ Solution (ver. 1) composition was also shown to be readily compatible with commercially available nucleic acid extraction kits. FIG. 1 illustrates RNA extraction results where the version 1 of PrimeStore™ Solution was used in conjunction with three commercially available kits: Qiagen Viral Mini, Ambion RNAqueous Mini, and Ambion A1/NCD MagMax. As illustrated by FIG. 1, when the lysis buffer of the extraction kit was replaced with the fixing formulation (denoted on the figure as "One-Step+), superior nucleic acid extraction was achieved when compared to extraction using kits according to standard protocol (denoted on the figure as "One-Step−". Extraction efficiency was measured by real time (r) reverse transcription (RT) polymerase chain reaction (PCR) [rRT-PCR].

FIG. 3 shows preservation of naked RNA in PrimeStore™ Solution compared to preservation in a prior solution, with water used as a control. As illustrated in FIG. 3, detection (by fluorescence) occurred at the earliest amplification cycle for RNA stored in PrimeStore™ Solution (ver. 1) at all time-points assayed.

Example 6

PrimeStore™ Solution for the Collection of Nasal Wash Specimens

A prospective clinical detection study was conducted using nasal wash specimens from: 1) symptomatic pediatric patients and 2) asymptomatic or symptomatic family members. Detection of influenza virus compared nasal wash specimens collected in PrimeStore™ Solution and Viral Transport Medium (VTM) by real-time RT-PCR (rRT-PCR) and traditional culture, respectively. Genetic characterization of influenza genes encoding hemagglutinin (HA), neuraminidase (NA), and matrix surface (MA) proteins were performed using select nasal wash specimens preserved in PrimeStore™ Solution to evaluate vaccine effectiveness and drug sensitivity within viral strains.

Influenza is a highly evolving, RNA-based respiratory virus responsible for more than 200,000 hospitalizations and about 36,000 fatalities each year in the United States. Widespread emergence of influenza drift variants among contemporary circulating human viruses prompted a change in all three vaccine components for the upcoming 2008/09 season. Increased morbidity and mortality during the 2007/08 season included 72 influenza-associated pediatric deaths and continued drug resistance (oseltamivir [TamiFlu®, Roche Laboratories, Inc., Nutley, N.J., USA] and adamantadine) within circulating strains.

Materials and Methods

A total of 100 pediatric (index) patients who met the clinical case criteria for influenza infection and 126 family contacts were enrolled in the study. Nasal washings were placed into PrimeStore™ Solution and Universal Viral Transport Medium (Becton-Dickinson, Franklin Lakes, N.J., USA) and analyzed by rRT-PCR or culture analysis, respectively. rRT-PCR was performed using influenza type (A or B) and sub-type (H3, H1, H5) specific primers/probes according to Daum et al. (2007). Further genetic characterization of selected clinical samples preserved in PrimeStore™ Solution was performed using standard RT-PCR and direct nucleotide sequencing of the hemagglutinin HA, NA, and MA viral proteins.

Results

Of the total samples evaluated (N=226; 100 index, 126 family contacts), 66 (29%) tested positive for influenza virus (45 H3N2, 2 H1N1 and 19 B) by rRT-PCR. rRT-PCR from nasal washings preserved in PrimeStore™ Solution detected influenza virus from 11 patients (9 Flu A and 2 Flu B) that were not detected by culture (Table 5 and Table 6). Of these 11 specimens, five were from patients enrolled as family contacts.

Phylogenetic analysis of influenza A and B HA genes exhibited drifting compared to the 2007/08 vaccine strains and revealed a higher genetic homology to the 2008/09 Brisbane vaccine strains. Some genetic differences in viruses were noted among family members, particularly among influenza A (H3N2) strains. MA analysis revealed adamantane resistance in all influenza A H3N2 strains, but sensitivity in both H1N1 viruses. All influenza B strains (n=18) were sensitive to the neuraminidase inhibitor drugs zanamivir (Relenza® GlaxoSmithKline, Research Triangle Park, N.C., USA) and oseltamivir (Tamiflu® Roche) based on the presence of an aspartic acid (D) at amino acid 197 (influenza B numbering) in the NA gene.

Real-Time RT-PCR vs. Culture rRT-PCR is superior to traditional culture for the detection of influenza virus from original nasal wash specimens preserved in PrimeStore™ solutions: influenza was detected within 2 hours (c.f. 2 to 7 days for conventional culture methods); and the analyses were more sensitive (11 specimens; 9 Flu A and 2 Flu B detected below culture limits). Moreover, the use of molecular diagnostic methods in lieu of conventional organism culture did not propagate potentially infectious viruses, and simultaneously provided the type and subtype of the influenza virus.

Genetic Analysis

Vaccine Relatedness

H3N2 Strains: Analysis of the HA1 gene of the influenza A (H3N2) hemagglutinin (HA) revealed genetic drift including five amino acid differences in all Texas strains compared to the 2007-08 A/Wisconsin/67/2005 vaccine strain. One HA1 mutation noted in all the Texas strains (D122N) is a potential glycosylation site. All A/Texas (H3N2) strains exhibited a greater HA homology (99.0-99.7%) to the newly selected 2008-09 A/Brisbane/10/2007 strain.

H1N1 Strains: The hemagglutinin HA1 gene of the 2 influenza A (H1N1) exhibited 7 amino acid changes compared to A/Solomon Island/3/2006 vaccine strain. Four substitutions (R90K, T145V, K210T and E290K) were within known H1 antibody combining sites. Both Texas H1N1 strains exhibited greater HA homology (98.8% and 99.4%) to the newly selected 2008-09 A/Brisbane/59/2007 vaccine strain.

Influenza B strains: Analysis of the HA1 hemagglutinin and neuraminidase genes revealed all Texas strains were of the B/Yamagata lineage and genetically more homologous to the 2008-09 B/Brisbane/5/2007 vaccine strain than the 2007/08 B/Malaysia/2506/2004 vaccine strain.

Family Mutation

Amino acid changes were noted in the NA, HAL M1 and M2e among family members. The HA1. Hemagglutinin showed the highest mutation of the influenza genes analyzed, with one family exhibiting five amino acid changes.

Analysis of the highly conserved 24 amino acid M2e viral surface proton pump showed some variation within families. One index patient strain contained 3 unique amino acid M2e substitutions that were 'wild-type' within family member strains.

Antiviral Susceptibility

Adamantane: Matrix gene (MA) genetic analysis, specifically a serine-to-asparagine substitution at position 31 (S31N), revealed adamantane resistance in all influenza A (H3N2) strains but sensitivity in both influenza A (H1N1) viruses.

Neuraminidase Inhibitors: All Texas influenza A (H3N2) isolates were shown to be sensitive to oseltamivir through genetic analysis of E119V, R292K, and N294S substitutions in the NA gene. Genetic analysis of the influenza B NA gene revealed that all Texas strains contained an aspartic acid (D) residue at position 197, and are thus likely sensitive to oseltamivir.

The protocols and tests herein can be adapted for other microbes like tuberculosis, malaria, *staphylococcus*, and the like and other pathogens where there is a need to know antimicrobial susceptibility quickly.

Example 7

Influenza Sample Collection Using PrimeStore™ Solution

The compositions of the present invention provide a single sample collection, transport, and storage reagent that facilitate: 1) procuring high quality nucleic acids from clinical or environmental specimens, 2) inactivation of potentially infectious biological pathogens for safe handling and transport of specimens, and 3) stabilization and preservation of released 'naked' RNA/DNA preventing hydrolysis/nuclease degradation for prolonged periods at ambient temperatures. The results of one such study are presented in the following example:

TABLE 5

Influenza Subtype Detection: rRT-PCR vs. Culture

| Total Flu A Samples | Influenza A | | Influenza B | | Total Flu B Samples |
|---|---|---|---|---|---|
| (N = 47) | rRT-PCR (N = 47) | Culture (N = 40) | rRT-PCR (N = 19) | Culture (N = 17) | (N = 19) |
| Index Patients (28) | 28/28 (100%) | 23/28 (82%) | 16/16 (100%) | 14/16 (88%) | Index Patients (16) |
| Family Contacts (19) | 19/19 (100%) | 15/19 (79%) | 3/3 (100%) | 3/3 (100%) | Family Contacts (3) |

TABLE 6

Positive Influenza Detection: rRT-PCR vs. Culture

| Total Samples (N = 226) | Flu Positive (N = 66) | rRT-PCR (N = 66) | Culture (N = 66) |
|---|---|---|---|
| Index Patients (100) | 44/100 | 39/39 (100%) | 37/39 (94%) |
| Family Contacts (126) | 22/126 | 27/27 (100%) | 18/27 (67%) |

This example illustrates the effectiveness of the PrimeStore™ Solution (ver. 2.2) in killing pathogenic microbe(s).

Methods

Real-time RT-PCR was used to assay influenza A (H5N1) virus nucleic acid preserved in PrimeStore™ Solution. A time-course study at room temperature was carried out to evaluate the integrity of clinical specimens, cloacal samples, and cloned template avian influenza A virus (H5) RNA stored and extracted from PrimeStore™ Solution, Viral Transport Media, RNA Storage Solution, or nuclease-free water. PrimeStore™ Solution extraction efficiency was compared to three commercially available nucleic acid extraction kits. Furthermore, the ability of RNA contained in PrimeStore™ Solution to resist nuclease degradation was evaluated.

Results

PrimeStore™ Solution (version 2, but lacking ethanol) inactivated microbial agents while preserving released RNA/DNA from clinical material, i.e., nasal washes, throat swabs, or environmental samples. Clinical specimens or environmental samples placed in this solution were stabilized at room temperature for up to 30 days while degradation of nucleic acids occurred in other transport media. PrimeStore™ Solution is compatible with commercially available RNA isolation kits and produced an increased nucleic acid yield.

Example 8

Killing of MRSA (ATCC33592) in PrimeStore™ Solution

Figure 6:
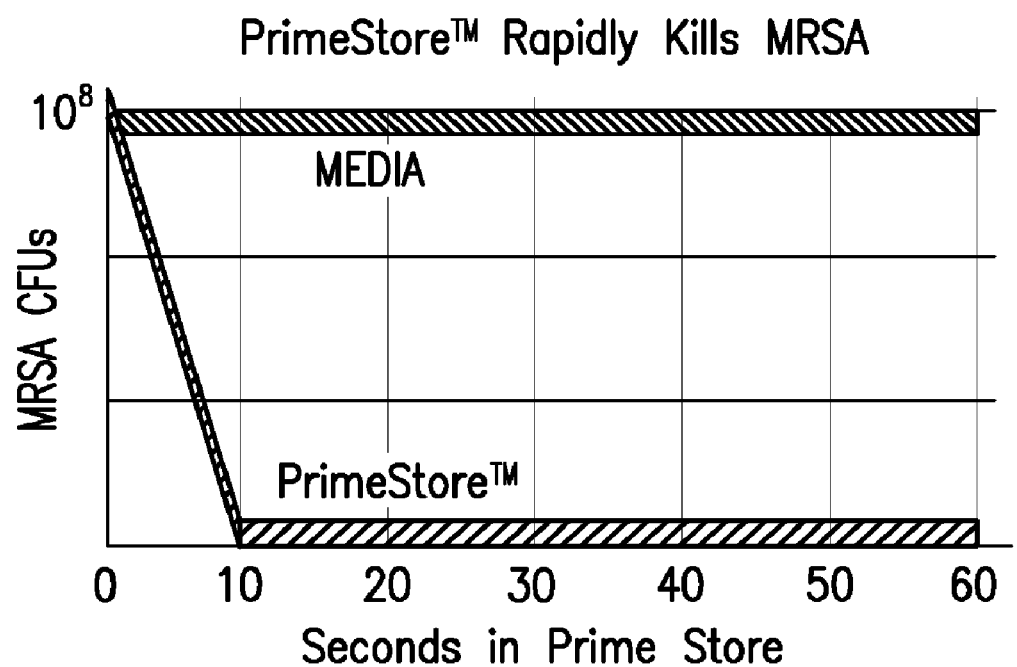
FIG. 6 illustrates the ability of PrimeStore™ Solution to rapidly kill microorganisms. Shown is a comparison of cell growth of MRSA either in culture medium (TSB), or in a solution of PS. After 10 seconds in PrimeStore™ Solution, no viable bacterial pathogens were detected.

This example illustrates the effectiveness of the PrimeStore™ Solution (ver. 2.2) in killing a potential bacterial contaminant. Methicillin-resistant *Staphylococcus aureus* (MRSA) strain ATCC33592 was diluted 10-fold and 1000-fold into PrimeStore™ Solution (Ver. 2.2) and quantitated (see FIG. 6).

Experimental Protocol
Day Procedure
   0 Transfer MRSA (ATCC33592) from a Culti-loop® (Remel) to 1.5 mL of TSB in a 15-ml conical test tube. Incubate at 37° C. for approximately 15 min. Gently vortex suspension and transfer 100 μL to a blood-agar plate. Incubate the plate overnight at 37° C.
   1 Observe heavy and uniform colony growth after 12 hr incubation. Transfer ~10% of colonies to 300 mL of tryptic soy broth (TSB) in a sterile, 1-liter flask. Place flask on shaker at 37° C. and 200 rpm.

After approximately 4-6 hrs' incubation, transfer ~50 mL of bacterial suspension to new 1-liter flask containing 300 mL fresh TSB.

After approximately 4-6 hrs' incubation, transfer ~100 μL of culture into 900 μL of TSB (1:10 control dilution). From this suspension 10 were transferred to 990 μL of TSB (1:1000 control dilution).

Transfer 100 μL, of culture into 900 μL of PrimeStore™ Solution (1:10 PrimeStore™ dilution). From this suspension 10 μL were transferred to 990 μL of TSB (1:1000 PrimeStore™ dilution).

Immediately after transfer into TSB or PrimeStore™ Solution (ver. 2.2), the suspensions were gently vortexed and 100 μL were plated from both dilutions of control and PrimeStore™ suspensions onto blood agar plates. The time-zero time point was actually about two minutes following addition of the bacteria to the TSB or PrimeStore™ Solution.

The suspensions in TSB and PrimeStore™ Solution (ver. 2.2) were kept at room temperature.

An additional 100 μL was plated onto blood agar plates at 5, 15, 30, 60, 120 and 240 minutes after the preparation of the suspensions in TSB and PrimeStore™ Solution.

Bacterial suspensions on the plates were allowed to dry, the plated inverted and the plates incubated overnight at 37° C.

A titration of the shaker culture was also performed by mixing 100 μL of the suspension from the shaker culture with 900 μL of TSB ($10^{-1}$ dilution). Serial 10-fold dilutions were prepared through $10^{-9}$. 100 μL samples were plated onto blood agar from all dilutions except $10^{-1}$.

Plates were observed for bacterial colonies. All plates were stored at 4° C. for later observation, if necessary.

Results

The results are presented in Table 7 and Table 8. Briefly, the bacterial suspension contained approximately $4.7 \times 10^9$ cfu/ml. Thus, the 1:10 dilution contained approximately $4.7 \times 10^8$ cfu/ml and the 1:1000 dilution contained $4.7 \times 10^6$ cfu/ml. At all time points, the bacteria suspended in TSB were too numerous to count. At all time points the bacteria suspended in PrimeStore™ Solution and plated onto blood agar plates had no detectable colonies.

TABLE 7

KILLING OF MRSA (ATCC 33592) BY PRIMESTORE ™ SOLUTION (VER. 2.2)

| Incubation Time | In TSB | | In Primestore | |
|---|---|---|---|---|
| (Minutes) | 1:10 | 1:1000 | 1:10 | 1:1000 |
| 0 | TNTC | TNTC | 0 | 0 |
| 5 | TNTC | TNTC | 0 | 0 |
| 15 | TNTC | TNTC | 0 | 0 |
| 30 | TNTC | TNTC | 0 | 0 |
| 60 | TNTC | TNTC | 0 | 0 |
| 120 | TNTC | TNTC | 0 | 0 |
| 240 | TNTC | TNTC | 0 | 0 |

TNTC = too numerous to count.

TABLE 8

TITRATION OF MRSA ATCC33592 FROM SUSPENSION CULTURE

| Dilution | CFU/plate | CFU/ml |
|---|---|---|
| 1.E+01 | TNTC | |
| 1.E+02 | TNTC | |
| 1.E+03 | TNTC | |
| 1.E+04 | TNTC | |
| 1.E+05 | TNTC | |
| 1.E+06 | TNTC | |
| 1.E+07 | 35 | $3.5 \times 10^9$ |
| 1.E+08 | 6 | $6 \times 10^9$ |
| 1.E+09 | 0 | |

NOTE:
CFU/ml calculations are corrected to include the plating volume of 0.1 mls
Final Conc: $4.7 \times 10^9$/ml
TNTC = too numerous to count.
CFU = colony forming units.

An additional study was performed to determine the time of exposure necessary for killing MRSA ATCC33592 when diluted 10-fold into PrimeStore™ Solution (Ver. 2.2), and to determine the effect of dilution of the bacteria after exposure to PrimeStore™ Solution, but before plating.

Experimental Protocol

Day Procedure

0 Transfer MRSA (ATCC33592) from TNTC plate from the study described above into 4 mL of TSB. These plates had been stored at 4° C. for approximately 48 hrs. Bacteria were vortexed gently and placed at room temperature for approximately 10 min. before use. 0.1 mL of bacterial suspension was transferred to 0.9 mL PrimeStore™ Solution and vortexed gently. After approximately 60 sec, the bacteria in PrimeStore™ were again vortexed gently and 0.1 mL of bacterial suspension was transferred into 0.3 mL of TSB (1:4 dilution). 100 μL, of bacteria in PrimeStore™ Solution (designated "neat") and from the 1:4 dilution into TSB were plated onto blood agar plates (5% sheep RBCs in TSA). This process was repeated at 5 and 15 min., and then again with dilutions made into TSB instead of PrimeStore™ Solution.

The liquid bacterial suspensions on the blood agar plates were allowed to dry at room temperature and then incubated overnight at 37° C.

1 After approximately 16 hrs. incubation, the plates were removed from the incubator and colonies counted.

Results

The bacterial suspension contained an unknown number of colony forming units (cfu) per mL. At all time points the bacteria suspended in tryptic soy broth (TSB) were too numerous to count (TNTC). At all timepoints the bacteria suspended in PrimeStore™ compositions and plated onto blood agar plates produced no colonies (Table 9).

TABLE 9

KILLING OF MRSA (ATCC33592) BY PRIMESTORE ™ SOLUTION

| Incubation Time | In TSB | | In TSB | |
|---|---|---|---|---|
| (minutes) | neat | 1:4 | neat | 1:4 |
| 1 | TNTC | TNTC | 0 | 0 |
| 5 | TNTC | TNTC | 0 | 0 |
| 15 | TNTC | TNTC | 0 | 0 |

TNTC = too numerous to count.

Example 9

Additional Studies Evaluating PrimeStore™ Solutions

Figure 7A:
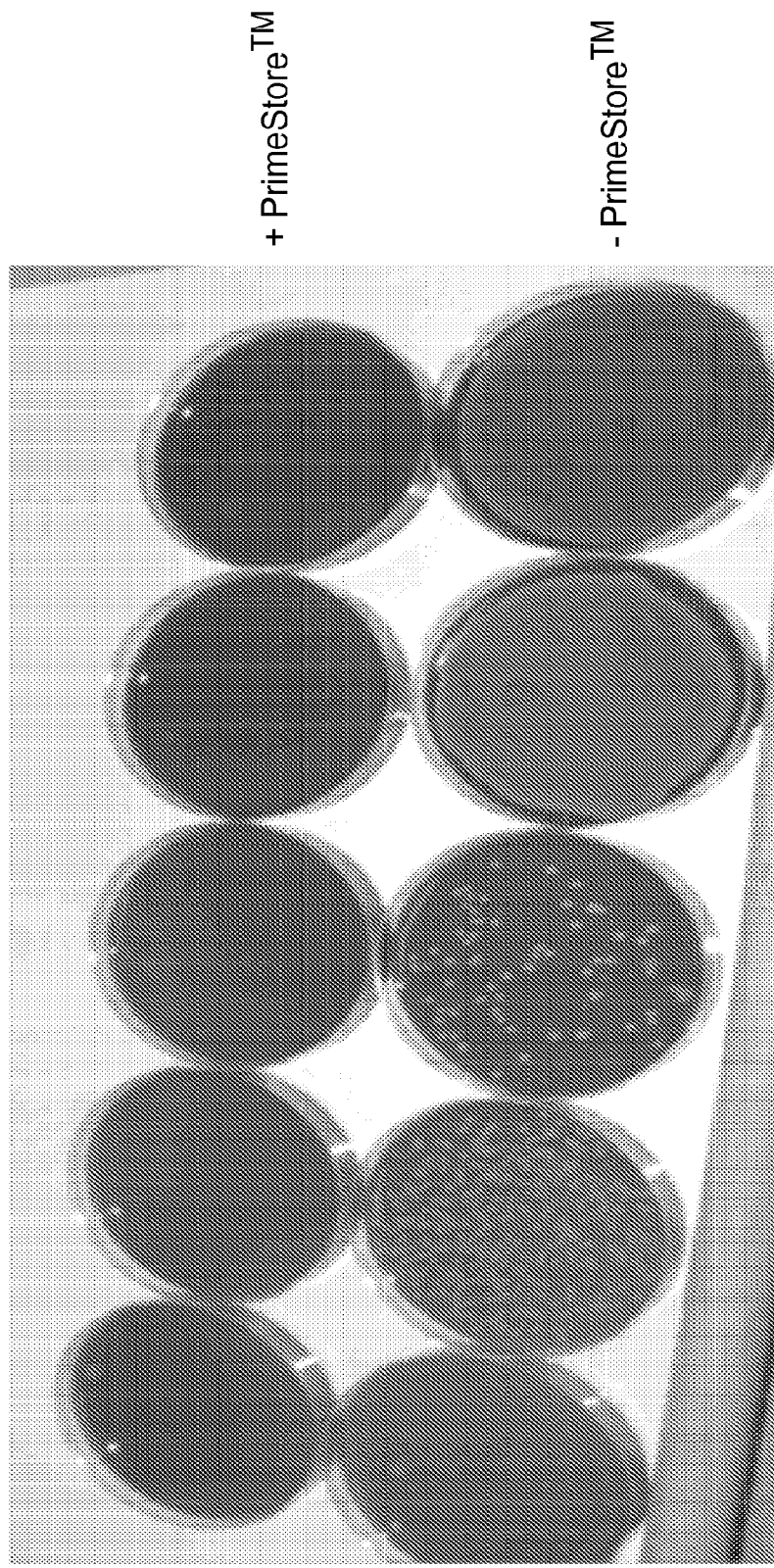
FIG. 7A shows the inactivation of chicken cloacal specimens in PrimeStore™ Solution (Ver. 1). PrimeStore™ Solution inactivates microbial agents in ≦1 hr. Four original chicken cloacal samples were immersed in PrimeStore™ Solution (top row) or water (bottom row) and subsequently plated on blood agar plates.
Figure 7B:
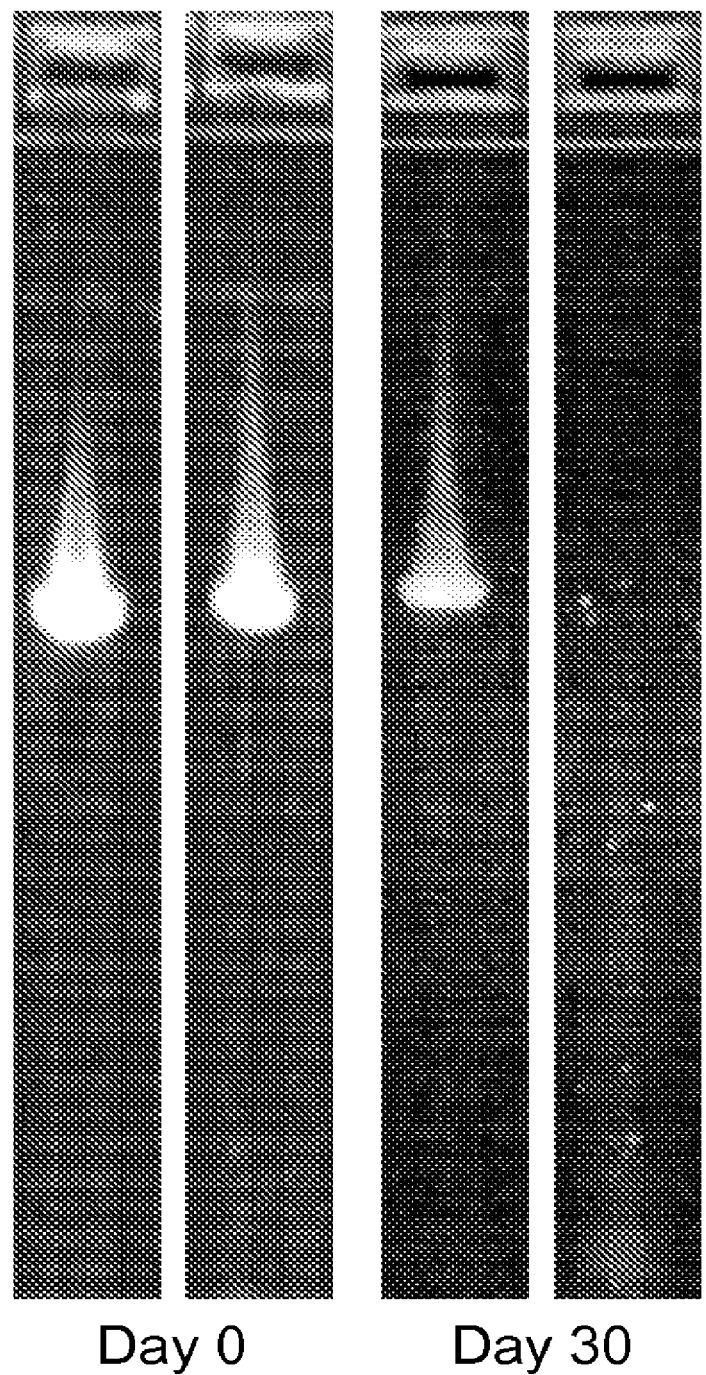
FIG. 7B demonstrates that PrimeStore™ inhibits RNA base hydrolysis for 30 days at room temperature. RNA was incubated at room temperature (22-26° C.) in PrimeStore™ (gel lane 1 and 3) and water (gel lane 2 and 4), and subsequently RT-PCR amplified (1500 base pairs) at Day 0 and Day 30. PrimeStore™ preserved collected RNA, and prevented RNA/DNA degradation at room temperature up to 30 days.

The data in FIG. 7B illustrate the ability of PSS to inactivate microbes. Shown is a study in which chicken cloacal specimens were collected in PrimeStore™ Solution (Ver. 1). PrimeStore™ Solution inactivated the microbial agents in $\leq 1$ hr. Four original chicken cloacal samples were immersed in PrimeStore™ Solution or water and subsequently plated on blood agar plates. These results showed that the disclosed composition could quickly kill or inactive microorganisms in the sample.

The data in FIG. 7C illustrate the ability of PSS to inhibit RNA base hydrolysis for 30 days at room temperature. RNA was incubated at room temperature (22-26° C.) in PrimeStore™ (gel lane 1 and 3) and water (gel lane 2 and 4), and subsequently RT-PCR amplified (1500 base pairs) at Day 0 and Day 30. PrimeStore™ preserved collected RNA, and prevented RNA/DNA degradation at room temperature up to 30 days (see also, e.g., Table 11).

Flu Inhibition Assay
The reagents for this assay include
Trypsin Medium:
45 mL Sterile N/C EMEM
3 mL stock 7.5% Na Bicarbonate (2%)
1.5 mL SPG (1%)
75 µL Trypsin (0.05%)
1.5 mL Fungizone (1%)
150 µL Gentamicin
Filter medium.
Crystal Violet: 150 ml glutaric dialdehyde
2 gm crystal violet
2850 mL deionized waterProtocols
Preparation of Serum Samples for Assay Thaw and vortex serum samples. For each sample, label the lid of a corresponding Spin-X tube. Combine 450 µL non-complete EMEM with 50 µL serum into a Spin-X tube. Warm tubes containing the sera and EMEM in a 56° C. water bath for 30 min. Centrifuge tubes at 8000 RPM for 2 min. at room temperature. Label and place samples into a −20° C. freezer until assayed.

Dilution Plates

Load 160 µl of each neat compound or serum sample into wells A1 through A12. Load the remaining wells with 120 µL, trypsin medium. Using a multi-channel pipette, draw 40 µL, of neat sample from row A and dilute into the corresponding wells in row B. Repeat dilution for each row, mixing well after each transfer. At row H, after mixing the transfer from row G, draw up 40 µL, from each well and discard. Obtain virus stock ($10^6$) from −80° C. freezer and thaw. Dilute virus stock in trypsin media to a $10^3$ dilution. After serial dilutions are completed, transfer 120 µL of influenza virus ($10^4$ $TCID_{50}$ per ml) to all wells in the dilution plate. This results in a total of 240 µL in all wells. Incubate dilution plate(s) at room temperature for 1 hour.

MDCK Cell Plates

Sterilize and place glass reservoir, comb dispenser and tubing inside the fume hood. Inside the hood, connect the tubing to the reservoir and fill nozzle of the comb. Connect the aspirator tube to the vacuum nozzle on the comb. Place the reservoir on an elevated surface and turn on the aspirator. Put PBS into the reservoir (1 L or more may be needed depending on the number of plates). Wash the cell plates 3× with the PBS comb (aspirate the medium, then press the button for roughly 1 second to wash the wells, repeat twice). Using a multi-channel pipette, transfer 50 µL from each well in column 1 of the dilution plate to columns 1 through 4 of the cell plate. Transfer 50 µL from each well in column 2 of the dilution plate to columns 5 through 8 of the cell plate. Transfer 50 µL from each well in column 3 to columns 9 through 12 of the cell plate. Repeat transfer to additional cell plates for remaining samples. Incubate cell plates for 1 hour at 37° C. After incubation period, add 50 µL trypsin medium to all wells of the cell plates. Return plates to incubation chamber, and incubate for 4 days post-infection.

Staining

Add 100 µL of Crystal Violet to all wells. Let sit for 1 hour. Rinse plates in cold running water and air dry.

TABLE 10

| 5 mM | 10 mM | 25 mM | 35 mM | 50 mM |
|---|---|---|---|---|
| TITRATION OF TCEP USING WHOLE INFLUENZA A VIRUS | | | | |
| 30.353 | 24.58 | 24.52 | 24.14 | 25.9582 |
| 30.2261 | 22.74 | 24.26 | 22.74 | 26.0337 |
| 30.28955 | 23.66 | 24.39 | 23.44 | 25.99595 |
| 0.089732 | 1.301076 | 0.183848 | 0.989949 | 0.053387 |
| Titration of TCEP Using H5 Avian ssRNA | | | | |
| 27.2 | 25.25 | 25.63 | 27.3 | 28.3039 |
| 26.73 | 24.89 | 25.36 | 27.62 | 26.6854 |
| 26.965 | 25.07 | 25.495 | 27.46 | 27.49465 |
| 0.33234 | 0.254558 | 0.190919 | 0.226274 | 1.144452 |

Time-Course Study of the Long-Term Stability of PrimeStore Compositions

The following data demonstrate the effectiveness of various PrimeStore compositions in preserving nucleic acid integrity over a thirty-day period with samples stored at room temperature. PrimeStore compositions have been compared to water alone, ethanol alone, commercial buffers such as VTM and AVL.

TABLE 11

30-DAY TIME-COURSE COMPARISON STUDY OF VARIOUS COMPOSITIONS

DAY 1

| VTM | Water | EtOH | AVL | PS-V1 (Year old) | PS-V1 (new lot) | PS-V2 | PS-V2.2 (w/EtOH) | |
|---|---|---|---|---|---|---|---|---|
| 27.0225 | 26.1403 | 18.4463 | 24.2698 | 24.2607 | 23.9524 | 23.4426 | 20.2102 | |
| 24.42 | 25.6044 | 18.3206 | 24.4789 | 24.3716 | 23.9615 | 23.7387 | 20.063 | |
| 25.72125 | 25.87235 | 18.4463 | 24.37435 | 24.31615 | 23.95695 | 23.59065 | 20.1366 | AVG |
| 1.840245 | 0.378939 | 0.088883 | 0.147856 | 0.0784181 | 0.006435 | 0.209374 | 0.10408612 | STDEV |

DAY 6

| VTM | Water | EtOH | AVL | PS-V1 (Year old) | PS-V1 (new lot) | PS-V2 | PS-V2.2 (w/EtOH) | |
|---|---|---|---|---|---|---|---|---|
| 29.1988 | 29.3053 | 27.4058 | 37.9226 | 27.2379 | 27.165 | 24.53 | 22.4887 | |
| 28.6799 | 28.7916 | 27.0781 | 40 | 26.4857 | 26.7658 | 24.4418 | 22.4676 | |
| 28.93935 | 29.04845 | 27.24195 | 38.9613 | 26.8618 | 26.9654 | 24.4859 | 22.47815 | AVG |
| 0.366918 | 0.363241 | 0.231719 | 1.468944 | 0.5318857 | 0.282277 | 0.062367 | 0.01491995 | STDEV |

DAY 12

| VTM | Water | EtOH | AVL | PS-V1 (Year old) | PS-V1 (new lot) | PS-V2 | PS-V2.2 (w/EtOH) | |
|---|---|---|---|---|---|---|---|---|
| 27.997 | 28.151 | 26.9011 | 40 | 30.8352 | 31.0478 | 25.8926 | 22.2074 | |
| 28.0062 | 28.2211 | 26.2139 | 38.0439 | 30.4502 | 30.1935 | 25.3037 | 22.0025 | |
| 28.0016 | 28.18605 | 26.5575 | 39.02195 | 30.6427 | 30.62065 | 25.59815 | 22.10495 | AVG |
| 0.006505 | 0.049568 | 0.485924 | 1.383172 | 0.2722361 | 0.604081 | 0.416415 | 0.14488618 | STDEV |

DAY 20

| VTM | Water | EtOH | AVL | PS-V1 (Year old) | PS-V1 (new lot) | PS-V2 | PS-V2.2 (w/EtOH) | |
|---|---|---|---|---|---|---|---|---|
| 27.9851 | 28.7713 | 27.1105 | 40 | 30.1844 | 27.193 | 25.7407 | 20.8364 | |
| 28.4067 | 27.7929 | 27.0105 | 40 | 30.2465 | 27.2274 | 25.6213 | 20.2843 | |
| 28.1959 | 28.2821 | 27.0605 | 40 | 30.21545 | 27.2102 | 25.681 | 20.56035 | AVG |
| 0.298116 | 0.691833 | 0.070711 | 0 | 0.0439113 | 0.024324 | 0.084429 | 0.39039365 | STDEV |

DAY 30

| VTM | Water | EtOH | AVL | PS-V1 (Year old) | PS-V1 (new lot) | PS-V2 | PS-V2.2 (w/EtOH) | |
|---|---|---|---|---|---|---|---|---|
| 29.23 | 31.9168 | 33.012 | 40 | 29.1993 | 30.2386 | 23.0589 | 20.9348 | |
| 29.9067 | 31.3252 | 32.3001 | 40 | 28.827 | 29.6081 | 22.9662 | 20.4973 | |
| 29.56835 | 31.621 | 32.65605 | 40 | 29.01315 | 29.92335 | 23.01255 | 20.71605 | AVG |
| 0.478499 | 0.418324 | 0.503389 | 0 | 0.2632559 | 0.445831 | 0.065549 | 0.30935922 | STDEV |

PS-V1 (year old) = One-year old PrimeStore Formulation (Ver. 1).
PS-V1 (new lot) = Fresh PrimeStore Formulation (Ver. 2).
PS-V2 = Fresh PrimeStore Formulation (Ver 2) (without ethanol).
PS-V2.2 (w/EtOH) = Fresh PrimeStore Formulation (Ver. 2.2) (i.e. with ethanol).

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims.

Accordingly, the exclusive rights sought to be patented are as described in the claims below.

What is claimed is:

1. A method for denaturing proteins, inactivating nucleases and killing pathogens in one step without degrading nucleic acid of a biological sample containing proteins, nucleases, and nucleic acid, and suspected to contain pathogens, comprising:

providing a mixture containing one or more chaotropes, one or more detergents, one or more reducing agents, one or more chelators, and one or more buffers, together present in an amount sufficient to denature proteins, inactivate nucleases, kill pathogens, and not degrade nucleic acid;

contacting the biological sample with the mixture which denatures proteins, inactivate nucleases, kill pathogens, and does not degrade nucleic acid of the biological sample; and detecting the presence and identity of or absence of the pathogens in the biological sample.

2. The method of claim 1, wherein the one or more chaotropes are present in an amount from about 0.5 M to about 6 M, the one or more detergents are present in an amount from about 0.1% to about 1% (wt./vol.); the one or more reducing agents are present in an amount from about 0.5 mM to about 0.3 M; the one or more chelators are present in an amount from about 0.01 mM to about 1 mM; and the one or more buffers are present in an amount from about 1 mM to about 1 M.

3. The method of claim 2, wherein the one or more chaotropes comprise guanidine thiocyanate, guanidine isocyanate, guanidine hydrochloride, or any combination thereof.

4. The method of claim 2, wherein the one or more detergents comprise sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof.

5. The method of claim 2, wherein the one or more reducing agents comprise 2-mercaptoethanol, tris(2-carboxyethyl)phosphine, dithiothreitol, dimethylsulfoxide, tris(2-carboxyethyl)phosphine, or any combination thereof.

6. The method of claim 2, wherein the one or more chelators comprise ethylene glycol tetra acetic acid, hydroxyethylethylenediaminetriacetic acid, diethylene triamine penta acetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof.

7. The method of claim 2, wherein the one or more buffers comprise tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl)methyl amino)propane, 4-(2-hydroxyethyl)-1-piperazine ethanesulfonic acid, 3-(N-morpholine)propanesulfonic acid, bicarbonate, phosphate, or any combination thereof.

8. The method of claim 2, wherein the mixture further comprises one or more short-chain alkanols present in an amount from about 1% to about 25% (vol./vol.).

9. The method of claim 8, wherein the one or more short-chain alkanols comprise methanol, ethanol, propanol, butanol, pentanol, hexanol, or any combination thereof.

10. The method of claim 2, wherein the mixture further comprises one or more surfactants or defoaming agents present in an amount from about 0.0001% to about 0.3% (wt./vol.).

11. The method of claim 10, wherein the one or more surfactants or defoaming agents comprise silicone polymer, polysorbate, antifoam A, Tween, or any combination thereof.

12. The method of claim 2, wherein the pathogens are influenza virus particles or influenza-infected cells, bacteria that causes tuberculosis or tuberculosis-infected cells.

13. The method of claim 1, wherein the mixture further comprises added naked RNA or DNA present in an amount of about 1 pg/mL to 1 µg/mL.

14. The method of claim 13, further comprising detecting the presence or absence of the added naked DNA or RNA.

15. The method of claim 2, wherein the mixture is buffered to a pH of from 5 to 7.

16. The method of claim 15, wherein the mixture is buffered to a pH of from about 6.4 to 6.9.

17. The method of claim 2, wherein the biological sample contains viral particles, virally infected cells, bacteria, bacterially infected cells, fungal organisms, animal cells, or plant cells.

18. The method of claim 17, wherein contacting comprises detectably liberating nucleic acid contained within the particles, cells or organisms of the biological sample.

19. The method of claim 18, wherein nucleic acid of the biological sample is detectable by PCR analysis.

20. The method of claim 19, wherein the nucleic acid of the biological sample remains detectable by PCR analysis after the mixture containing the biological sample is stored at a temperature of 4C or more for a period of at least 14 days.

21. The method of claim 20, wherein about 5% or less of the nucleic acids of the biological sample are degraded after the mixture containing the biological sample is stored at a temperature of 12C or more for a period of at least 14 days.

22. The method of claim 19, wherein the nucleic acid of the biological sample remains detectable by PCR analysis after the mixture containing the biological sample is stored at a temperature of 4C or more for a period of at least 30 days.

23. The method of claim 22, wherein the nucleic acid of the biological sample remains detectable by PCR analysis after the mixture containing the biological sample is stored at a temperature of 12C or more for a period of at least 30 days.

24. A method for denaturing proteins, inactivating nucleases and killing pathogens in one step without degrading nucleic acid of a biological sample containing proteins, nucleases, and nucleic acid, and suspected to contain pathogens, comprising:

providing a mixture containing one or more chaotropes, one or more detergents, one or more reducing agents, one or more chelators, one or more buffers, one or more short-chain alkanols, and one or more surfactants, together present in an amount sufficient to denature proteins, inactivate nucleases, kill pathogens, and not degrade nucleic acid;

contacting the biological sample with the mixture which denatures proteins, inactivate nucleases, kill pathogens, and does not degrade nucleic acid of the biological sample, and detecting the presence and identity of or absence of the pathogens in the biological sample, wherein, said one or more chaotropes are selected from the group consisting of guanidine thiocyanate, guanidine isocyanate, guanidine hydrochloride, and any combination thereof; said one or more detergents are selected from the group consisting of sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, and any combination thereof;

said one or more chelators are selected from the group consisting of ethylene glycol tetra acetic acid, hydroxyethylethylenediaminetriacetic acid, diethylene triamine penta acetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, and any combination thereof; and said one or more buffers are selected from the group consisting of tris(hydroxymethyl)aminomethane, citrate, 2-(N-morpholino)ethanesulfonic acid, N,N-Bis(2-hydroxyethyl)-2-aminoethanesulfonic acid, 1,3-bis(tris (hydroxymethyl)methyl amino)propane, 4-(2-hydroxyethyl)-1-piperazine ethanesulfonic acid, 3-(N-morpholino) propanesulfonic acid, bicarbonate, phosphate, and any combination thereof; and said one or more short-chain alkanols are selected from the group consisting of methanol, ethanol, propanol, butanol, pentanol, or hexanol, and any combination thereof;

which are together present in an amount sufficient to denature proteins, inactivate nucleases; kill pathogens, and not substantially degrade nucleic acid of the biological sample upon contacting the mixture.

25. The method of claim 24, wherein:
the one or more chaotropes are present in an amount from about 0.5 M to about 6 M;
the one or more detergents are present in an amount from about 0.1% to about 1% (wt./vol.);
the one or more reducing agents are present in an amount from about 0.5 mM to about 0.3 M;
the one or more chelators are present in an amount from about 0.01 mM to about 1 mM;
the one or more buffers are present in an amount from about 0.0001% to about 0.3% (wt./vol.);
the one or more short-chain alkanols are present in an amount from about 1 to about 25% (vol./vol.); and
the one or more surfactants are present in an amount from about 0.0001% to about 0.3%.

26. The method of claim 25, wherein the mixture further contains naked RNA or DNA that has a predetermined nucleic acid sequence as an internal positive control that is detectable by PCR analysis.

27. The method of claim 25, wherein the pathogens are influenza virus particles or influenza virus-infected cells, bacteria that causes tuberculosis or tuberculosis-infected cells.

28. The method of claim 25, wherein the biological sample contains whole blood, plasma, serum, sputum, urine, stool, a white blood cell, a red blood cell, buffy coat, tears, mucus, saliva, semen, vaginal fluid, lymphatic fluid, amniotic fluid, spinal or cerebrospinal fluid, a peritoneal effusion, a pleural effusion, an exudate, a punctuate, an epithelial smear, a biopsy, a bone marrow sample, fluid from a cyst or an abscess, synovial fluid, vitreous or aqueous humor, an eye wash or aspirate, a pulmonary lavage or lung aspirate, or any combination thereof.

29. A method for denaturing proteins, inactivating nucleases and killing pathogens in one step without degrading nucleic acid of a biological sample containing proteins, nucleases, and nucleic acid comprising:
providing a mixture containing one or more chaotropes, one or more detergents, one or more reducing agents, one or more chelators, and one or more buffers, together present in an amount sufficient to denature proteins, inactivate nucleases, kill pathogens, and not degrade nucleic acid;
providing the biological sample suspected to contain pathogens;
contacting the biological sample with the mixture which liberates nucleic acid of the pathogens for PCR analysis;
PCR amplifying the nucleic acid, if present; and
determining the presence or absence of the pathogens in the biological sample.

30. The method of claim 29, wherein the one or more chaotropes are present in an amount from about 0.5 M to about 6 M, the one or more detergents are present in an amount from about 0.1% to about 1% (wt./vol.); the one or more reducing agents are present in an amount from about 0.5 mM to about 0.3 M; the one or more chelators are present in an amount from about 0.01 mM to about 1 mM; the one or more buffers are present in an amount from about 100 mM to about 1M and the pH of the mixture is about 6.2 to 6.9.

31. A method for denaturing proteins, inactivating nucleases and killing pathogens in one step without degrading nucleic acid of a biological sample containing proteins, nucleases, and nucleic acid, and suspected to contain pathogens, comprising:
providing a mixture containing one or more chaotropes, one or more detergents, one or more reducing agents, one or more chelators, and one or more buffers, together present in an amount sufficient to denature proteins, inactivate nucleases, kill pathogens, and not degrade nucleic acid, wherein the one or more chaotropes are present in an amount from about 0.5 M to about 6 M, the one or more detergents are present in an amount from about 0.1% to about 1% (wt./vol.); the one or more reducing agents are present in an amount from about 0.5 mM to about 0.3 M; the one or more chelators are present in an amount from about 0.01 mM to about 1 mM; and the one or more buffers are present in an amount from about 1 mM to about 1M.

32. The method of claim 31, wherein the one or more chaotropes comprise guanidine thiocyanate, guanidine isocyanate, guanidine hydrochloride, or any combination thereof; the one or more detergents comprise sodium dodecyl sulfate, lithium dodecyl sulfate, sodium taurodeoxycholate, sodium taurocholate, sodium glycocholate, sodium deoxycholate, sodium cholate, sodium alkylbenzene sulfonate, N-lauroyl sarcosine, or any combination thereof; the one or more reducing agents comprise 2-mercaptoethanol, tris(2-carboxyethyl) phosphine, dithiothreitol, dimethylsulfoxide, tris(2-carboxyethyl)phosphine, or any combination thereof; the one or more chelators comprise ethylene glycol tetra acetic acid, hydroxyethylethylenediaminetriacetic acid, diethylene triamine penta acetic acid, N,N-bis(carboxymethyl)glycine, ethylenediaminetetraacetic, citrate anhydrous, sodium citrate, calcium citrate, ammonium citrate, ammonium bicitrate, citric acid, diammonium citrate, ferric ammonium citrate, lithium citrate, or any combination thereof; the one or more buffers comprise tris(hydroxymethyl)aminomethane, citrate, 2-(N-morpholino)ethanesulfonic acid, N,N-Bis(2-hydroxyethyl)-2-aminoethanesulfonic acid, 1,3-bis(tris(hydroxymethyl) methyl amino)propane, 4-(2-hydroxyethyl)-1-piperazine ethanesulfonic acid, 3-(N-morpholino) propanesulfonic acid, bicarbonate, phosphate, or any combination thereof; and the mixture is buffered to a pH of from about 5 to 7.

33. The method of claim 31, wherein the mixture is buffered to a pH of from about 6.4 to 7.0.

34. The method of claim 31, further comprising contacting the biological sample with the mixture which denatures proteins, inactivate nucleases, kill pathogens, and does not degrade nucleic acid of the biological sample.

35. The method of claim 34, wherein contact with the composition is performed in one vessel and, after contact, the biological sample is non-infectious for transport.

36. The method of claim 35, wherein the contacted biological sample does not require refrigeration for subsequent detection of the presence or absence of pathogens.

37. The method of claim 36, wherein detection of the presence and identity of or absence of the pathogens can be determined for at least 7 days after contact with the mixture.

38. The method of claim 35, wherein the contacted biological sample is at an ambient temperature for a period of time prior to the detection of the presence or absence of pathogens.

39. The method of claim 38, wherein the period of time is at least 48 hours.

40. The method of claim 31, wherein the mixture further comprises one or more short-chain alkanols present in an amount from about 1% to about 25% (vol./vol.); one or more surfactants or defoaming agents present in an amount from about 0.0001% to about 0.3% (wt./vol.); and added naked RNA or DNA present in an amount of about 1 pg/mL to 1 µg/mL.

41. The method of claim 40, wherein the one or more short-chain alkanols comprise methanol, ethanol, propanol, butanol, pentanol, hexanol, or any combination thereof; and the one or more surfactants or defoaming agents comprise silicone polymer, polysorbate, antifoam A, Tween, or any combination thereof.

42. The method of claim 40, further comprising detecting the presence or absence of the added naked DNA or RNA.

* * * * *

UNITED STATES PATENT AND TRADEMARK OFFICE
CERTIFICATE OF CORRECTION

| | | |
|---|---|---|
| PATENT NO. | : 8,293,467 B2 | Page 1 of 1 |
| APPLICATION NO. | : 13/332204 | |
| DATED | : October 23, 2012 | |
| INVENTOR(S) | : Fischer et al. | |

It is certified that error appears in the above-identified patent and that said Letters Patent is hereby corrected as shown below:

In the first sentence of column 1, lines 8-9, in the section entitled "Cross-Reference to Related Applications," please delete "U.S. application Ser. No. 12/243,949, Oct. 1, 1998" and insert therefore --U.S. application Ser. No. 12/243,949, Oct. 1, 2008--

Signed and Sealed this
Twenty-second Day of January, 2013

David J. Kappos
*Director of the United States Patent and Trademark Office*